(12) United States Patent
Bitar

(10) Patent No.: US 10,377,985 B2
(45) Date of Patent: Aug. 13, 2019

(54) NEURAL PROGENITOR CELL DIFFERENTIATION

(71) Applicant: Wake Forest University Health Sciences, Winston-Salem, NC (US)

(72) Inventor: Khalil Bitar, Winston-Salem, NC (US)

(73) Assignee: WAKE FOREST UNIVERSITY HEALTH SCIENCES, Winston-Salem, NC (US)

(*) Notice: Subject to any disclaimer, the term of this patent is extended or adjusted under 35 U.S.C. 154(b) by 17 days.

(21) Appl. No.: 15/875,717

(22) Filed: Jan. 19, 2018

(65) Prior Publication Data
US 2018/0155684 A1  Jun. 7, 2018

Related U.S. Application Data

(62) Division of application No. 14/216,391, filed on Mar. 17, 2014, now Pat. No. 9,896,656.

(60) Provisional application No. 61/788,285, filed on Mar. 15, 2013.

(51) Int. Cl.
| | | |
|---|---|---|
| C12N 5/00 | (2006.01) | |
| C12N 5/02 | (2006.01) | |
| C12N 5/0793 | (2010.01) | |
| C12N 5/079 | (2010.01) | |
| A61K 35/30 | (2015.01) | |
| A61K 35/34 | (2015.01) | |

(52) U.S. Cl.
CPC ........... *C12N 5/0619* (2013.01); *A61K 35/30* (2013.01); *A61K 35/34* (2013.01); *C12N 5/0622* (2013.01); *C12N 2502/1347* (2013.01); *C12N 2533/52* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | |
|---|---|---|
| 6,419,920 B1 | 7/2002 | Mineau-Hanschke |
| 2003/0113812 A1 | 6/2003 | Hemperly |
| 2006/0153815 A1 | 7/2006 | Seyda et al. |
| 2007/0128171 A1 | 6/2007 | Tranquillo et al. |
| 2007/0269481 A1 | 11/2007 | Li et al. |
| 2007/0275362 A1 | 11/2007 | Edinger |
| 2011/0151011 A1 | 6/2011 | Flynn |

FOREIGN PATENT DOCUMENTS

| | | |
|---|---|---|
| WO | 0149827 A1 | 7/2001 |
| WO | 03029418 A2 | 4/2003 |
| WO | 2011059920 A2 | 5/2011 |

OTHER PUBLICATIONS

Evers et al., Is there a nitrergic modulation of the rat external anal sphincter?, Exp Physiol vol. 98.2 (2013): 397-404.
Extended Supplementary European Search Report for 14763675.7, dated Aug. 12, 2016; 9 pages.
Keef et al., Functional role of vasoactive intestinal polypeptide in inhibitory motor innervation in the mouse internal anal sphincter. J Physiol. Mar. 15, 2013;591(6):1489-506.
Office Action from related U.S. Appl. No. 14/777,335, dated Apr. 13, 2016; 18 pages.
Office Action from related U.S. Appl. No. 14/777,335, dated Oct. 31, 2016; 15 pages.
Orlando, et al., Regenerative medicine as applied to solid organ transplantation: current status and future challenges. Transpl Int. Mar. 2011;24(3):223-232.
Raghavan et al., Successful implantation of bioengineered, intrinsically innervated, human internal anal sphincter. Gastroenterology. Jul. 2011;141(1):310-319.
Raghavan et al., Neuroglial differentiation of adult enteric neuronal progenitor cells as function of extracellular matrix composition. Biomaterials. Sep. 2013;34(28):6649-6658.
Geisbauer, C.L., et al. Transplantation Of Enteric Cells Into The Rodent Stomach With Basic Fibroblast Growth Factor, Cell Science & Therapy, vol. 2; pp. 1-6 (2011).
Raghavan, S. et al. Bioengineered Three-Dimensional Physiological Model Of Colonic Longitudinal Smooth Muscle In Vitro. Tissue Engineering Part C: Methods, vol. 16; pp. 999-1009 (Oct. 2010).
Ward, Sean, M. et al. "Interstitial Cells Of Cajal Mediate Cholinergic Neurotransmission From Enteric Motor Neurons", The Journal of Neuroscience, vol. 20, No. 4, pp. 1393-1403 (Feb. 15, 2000).
Hansen, Ryan R. et al. "Characterization of Collagen Thin Films For Von Willebrand Factor Binding And Platelet Adhesion" Langmuir, vol. 27, pp. 13646-13656 (Oct. 3, 2011).

(Continued)

*Primary Examiner* — Julie Wu
*Assistant Examiner* — Douglas F White
(74) *Attorney, Agent, or Firm* — Nelson Mullins Riley & Scarborough LLP; Thomas J. Engellenner; Reza M. Mollaaghababa

(57) ABSTRACT

Differentiation and stability of neural stem cells can be enhanced by in vitro or in vivo culturing with one or more extracellular matrix (ECM) compositions, such as collagen I, IV, laminin and/or a heparan sulfate proteoglycan. In one aspect of the invention, adult mammalian enteric neuronal progenitor cells can be induced to differentiate on various substrates derived from components or combinations of neural ECM compositions. Collagen I and IV supported neuronal differentiation and extensive glial differentiation individually and in combination. Addition of laminin or heparan sulfate to collagen substrates unexpectedly improved neuronal differentiation, increasing neuron number, branching of neuronal processes, and initiation of neuronal network formation. In another aspect, neuronal subtype differentiation was affected by varying ECM compositions in hydrogels overlaid on intestinal smooth muscle sheets. The matrix compositions of the present invention can be used to tissue engineer transplantable innervated GI smooth muscle constructs to remedy agangli-onic disorders.

12 Claims, 18 Drawing Sheets

(56) References Cited

OTHER PUBLICATIONS

Bagyanszki, M. et al. "Diabetes-Related Alterations In The Enteric Nervous System And Its Microenvironment", World Journal of Diabetes, vol. 3, pp. 80-93 (May 15, 2012).
Fujimiya, M. et al. "Peptidergic Regulation of Gastrointestinal Motility in Rodents" Peptides, vol. 21, pp. 1565-1582 (Oct. 2000).
Dahm, L.M. et al. "Substance P Resonsiveness Of Smooth Muscle Cells Is Regulated By The Integrin Ligand, Thrombospondin", Proc. Natl. Acad. Sci. USA, vol. 93, pp. 1276-1281 (Feb. 6, 1996).
Tulla, M. et al. "Selective Binding Of Collagen Subtypes By Integrin Alpha 1-I, Alpha 2I, and Alpha 10-I Domains" The Journal of Biological Chemistry, vol. 276, pp. 48206-48212 (Sep. 25, 2001).
Raghavan, S. et al. "The Influence of Extracellular Matrix Composition On The Differntiation Of Neuronal Subtypes In Tissue Engineered Innervated Intestinal Smooth Muscle Sheets", Biomaterials, vol. 35, pp. 7429-7440 (Jun. 11, 2014).
International Search Report and Written Opinion for corresponding PCT/US2014/30456 dated Aug. 29, 2014.

NEURAL PROGENITOR CELL DIFFERENTIATION

RELATED APPLICATIONS

This application is a division of U.S. patent application Ser. No. 14/216,391 and is based upon and claims the priority of U.S. Provisional Application Ser. No. 61/788,285 filed Mar. 15, 2013, entitled "Neuroglial Differentiation," both of which are hereby incorporated in their entireties by reference.

GOVERNMENT RIGHTS

This invention was made with U.S. government support by the National Institutes of Health Grant Nos. RO1DK071614 and RO1DK042876. The U.S. government has certain rights in the invention.

TECHNICAL FIELD

The field of this invention is tissue engineering and, in particular, re-innervation of organs and body tissue.

BACKGROUND

An uninterrupted enteric nervous system with the preservation of myenteric ganglia is required for intestinal motility and function. Motor neurons of the myenteric ganglia predominantly express acetylcholine/tachykinins (excitatory) or nitric oxide/inhibitory peptides/purines (inhibitory) to mediate smooth muscle contraction and relaxation. Partial, selective, or total loss of nerve function and/or loss of nerve cell populations within organs and other body structures are characteristic of numerous diseases and disorders. For example, aganglionosis of various lengths of distal gut is the central pathology in Hirschsprung's disease. Enteric neuropathy is also secondary to several other disorders (e.g., diabetes, Parkinson's disease, and inflammation) resulting in gastrointestinal dysfunction. Gastrointestinal motor function is controlled by the intramural enteric nervous system. It is a complex interplay between the smooth muscle of the muscularis externa and the two enteric neuronal plexi.

Neural stem cell therapy is an emerging therapy that aims to reinstate neuronal function and thus gastrointestinal motor function by repopulating the enteric plexi. The research is driven by two significant findings: i) neural stem cells can be isolated from adult mammalian gut, including the ganglionated colon of Hirschsprung's patients; and ii) neural stem cells can be induced to differentiate into several neuronal subtypes and glia characteristic of the enteric nervous system (ENS) upon transplantation into explant cultures of aganglionic/aneural gut, or in vivo into distal colo-rectums in animal models.

While neural-crest derived enteric neural stem cells have been isolated from adult mammalian guts, including ganglionic bowel of patients with Hirschsprung's disease, there is little information or understanding of microenvironment-driven differentiation, and only limited studies describing subsequent functional behavior of these differentiated neurons in vitro. Moreover, restoration of nerve functions by neural stem cell transplantations as a treatment for nerve-loss associated disorders has not yet been clinically demonstrated, and there exists a need for methods and materials to support neuroglial cells, and to ensure phenotypic stability and long term survival of transplanted or implanted neural stem cells.

SUMMARY

It has been discovered that extracellular matrix (ECM) compositions can modulate neural stem cell fate and direct differentiation. The term "extracellular matrix" or "ECM" is used herein to denote composition comprising one or more of the following: collagen I, collagen IV, laminin, heparan sulfate, or fragments of one or more of such proteins.

One aspect of the invention includes a method of biasing neural stem cell differentiation having the steps of obtaining a population of smooth muscle cells, culturing the smooth muscle cells to form a uniaxially-aligned smooth muscle sheet, obtaining a population of neural stem cells, culturing the neural stem cells in a hydrogel, wherein the hydrogel is applied to the uniaxially-aligned smooth muscle sheet, and exposing the neural stem cells to at least one extracellular matrix (ECM) component, wherein the ECM component biases differentiation of the neural stem cells into differentiated neural stem cells that are enriched for a neuronal subtype. For example, the neuronal subtype are cholinergic neurons, where the hydrogel can include collagen I, or at least at least about 800 µg/ml collagen I, or between about 800 µg/ml and about 1600 µg/ml collagen I. In another example, the neuronal subtype are nitrergic neurons, where the hydrogel can include collagen IV and be substantially free of laminin, or at least about 200 µg/ml collagen IV and be substantially free of laminin. In another example, the neuronal subtype are peptidergic neurons, where the hydrogel can include collagen I, collagen IV, and laminin, or at least about 800 µg/ml collagen I, at least about 200 µg/ml collagen IV, and at least about 5 µg/ml laminin. Another aspect of the invention can include isolating the differentiated neural stem cells and administering the differentiated neural stem cells to a patient. For example, the administering can include injecting, into the patient, the differentiated stem cells in the hydrogel. In another example, the differentiated neural stem cells innervate the uniaxially-aligned smooth muscle sheet to form an innervated smooth muscle sheet and can include the additional step of implanting the innervated smooth muscle sheet into a patient.

Another aspect of the invention includes a method of biasing neural stem cell differentiation having the steps of obtaining a population of neural stem cells, obtaining a population of smooth muscle cells, culturing the neural stem cells in the presence of the smooth muscle cells, wherein the neural stem cells adhere on a substrate with a substrate coating comprising at least one extracellular matrix (ECM) component, wherein the ECM component biases differentiation of the neural stem cells into differentiated neural stem cells that are enriched for neurons. For example, the substrate coating comprises at least one of laminin, collagen I, and collagen IV, or the substrate coating comprises laminin, and at least one of collagen I and collagen IV, or the substrate coating comprises collagen I and collagen IV, and at least one of laminin and heparan sulfate. Another aspect of the invention can also include isolating the differentiated neural stem cells and administering the differentiated neural stem cells to a patient. For example, the administering can include injecting the differentiated neural stem cells into the patient.

Another aspect of the invention includes a method of biasing neural stem cell differentiation by obtaining a population of neural stem cells, obtaining a population of smooth muscle cells, culturing the neural stem cells in the presence of the smooth muscle cells, wherein the neural stem cells adhere on a substrate with a substrate coating comprising at least one extracellular matrix (ECM) component, wherein the ECM component biases differentiation of the neural stem cells into differentiated neural stem cells that are enriched for glial cells. For example, the substrate coating can include at least collagen I and collagen IV, and be substantially free of at least one of laminin and heparan sulfate, or the substrate coating can comprises at least 5 μg/cm2 collagen I and at least 5 μg/cm2 collagen IV, and be substantially free of at least one of laminin and heparan sulfate. Another aspect further includes the step of isolating the differentiated neural stem cells and administering the differentiated neural stem cells to a patient. For example, the administering comprises injecting the differentiated neural stem cells into the patient.

In one aspect of the invention, adult mammalian enteric neural progenitor cells can be induced to differentiate on various substrates derived from components or combinations of ECM compositions. Neuronal and glial differentiation was studied as a function of ECM composition. Collagen I and collagen IV substrates supported neuronal differentiation and extensive glial differentiation individually and in combination. The addition of laminin or heparan sulfate to collagen substrates improved neuronal differentiation, increasing the number of neurons and the branching of neuronal processes and initiation of neuronal network formation. Various neural ECM components were evaluated individually and in combination to study their effect of neuroglial differentiation of adult enteric neural progenitor cells.

In another aspect of the invention, tissue-engineered intestinal longitudinal smooth muscle sheets can be innervated using enteric neuronal progenitor cells embedded with hydrogels of varying ECM composition. Differentiated neuronal composition (cholinergic, nitrergic, peptidergic), as well as functional neuronal physiology mediating smooth muscle contraction/relaxations, were evaluated. Several functional differentiated neuronal subtypes were present in tissue-engineered intestinal sheets, capable of mediating smooth muscle contraction/relaxation. Neuronal populations varied from being highly cholinergic (collagen I), highly nitrergic (composite collagen I and collagen IV), or balanced between the two (composite collagen I and collagen IV, and laminin and/or heparan sulfate). Additionally, an increase in peptidergic neurons was detected with laminin and heparan sulfate.

The feasibility of transplantation of various types of neuronal progenitor cells (CNS-derived, neural tube-derived, embryonic and adult ENS-derived) in explant cultures of aneural gut is well established. However, conditions required for successful engraftment and long-term survival, focusing on a permissive environment heretofore have not been identified. Studies related to in vitro differentiation of adult enteric neuronal progenitor cells with a focus on the role of the ECM can help optimize the survivability and maintenance of both neuronal and neuroglial phenotypes. Moreover, our studies indicate that neuronal differentiation can be modulated by varying the composition of ECM microenvironments. Enriched populations of differentiated neuronal subtypes can be derived within transplantable tissue engineered sheets, using ECM microenvironments. ECM microenvironments may also facilitate adequate trophic support and phenotype maintenance of differentiated neurons.

In certain embodiments, neural differentiation is induced by administering an effective amount of laminin or a composition comprising laminin, including fragments, derivatives, or analogs thereof. In a specific example, the laminin can be a complete laminin protein. In further examples, the laminin is selected from laminin-1, laminin-2, laminin-4, and fragments or combinations thereof. In further examples, the laminin or laminin composition includes a substance at least substantially homologous to laminin-1, laminin-2, or laminin-4. In yet further implementations, the laminin or laminin composition comprises a polypeptide at least substantially homologous to the laminin α1 chain, e.g., having at least 80%, or 85%, or 90%, or 95% sequence identical to at least a fragment of the laminin α1 chain that retains the capacity to induce neuroglial differentiation.

Amounts effective for various therapeutic treatments of the present disclosure may, of course, depend on the severity of the disease and the weight and general state of the subject, as well as the absorption, inactivation, and excretion rates of the therapeutically-active compound or component, the dosage schedule, and amount administered, as well as other factors known to those of ordinary skill in the art. It also should be apparent to one of ordinary skill in the art that the exact dosage and frequency of administration will depend on the particular laminin, laminin composition, or other therapeutic substance being administered, the particular condition being treated, the severity of the condition being treated, the age, weight, general physical condition of the particular subject, and other medication the subject may be taking. Typically, dosages used in vitro may provide useful guidance in the amounts useful for in vivo administration of the pharmaceutical composition, and animal models may be used to determine effective dosages for treatment of particular disorders. For example, animal models of neural disorders may be used to determine effective dosages that can then be translated to dosage amount for other subjects, such as humans, as known in the art. Various considerations in dosage determination are described, e.g., in Gilman et al., eds., Goodman And Gilman's: The Pharmacological Bases of Therapeutics, 8th ed., Pergamon Press (1990); and Remington's Pharmaceutical Sciences, 17th ed., Mack Publishing Co., Easton, Pa. (1990), which is herein incorporated by reference.

In another example, the laminin or laminin composition can be introduced into an in vitro culture of neural stem cells (or co-administered with neural stem cells to a subject) in an amount sufficient to provide a dose of laminin of between about 10 fmol/g and about 500 nmol/g, such as between about 2 nmol/g and about 20 nmol/g or between about 2 nmol/g and about 10 nmol/g. In additional examples, the laminin or laminin composition can be provided in vitro or administered to a subject in an amount sufficient to provide a dose of laminin of between about 0.01 μg/kg and about 1000 mg/kg or between about 0.1 mg/kg and about 1000 mg/kg, in particular examples this amount is provided per day or per week. In another example, the laminin or laminin composition is administered to a subject in an amount sufficient to provide a dose of laminin of between about 0.2 mg/kg and about 2 mg/kg. In further examples, the laminin or laminin composition is administered to a subject in an amount sufficient to provide a concentration of laminin in the administrated material of between about 5 nM and about 500 nM, such as between about 50 nM and about 200 nm, or about 100 nM.

Addition of heparan sulfate to composite collagen mixtures can improve neuronal differentiation as well. Neuronal networking and neuronal clustering was visible at the later time point. Heparan sulfate and its interaction with glial cell-derived neurotrophic factor (GDNF) and other neurotrophic factors stabilizes and makes these factors locally available, possibly modulating neurite outgrowth and neuronal differentiation. Heparan sulfate interacts with both collagen IV and with laminin, to positive modulate neuronal differentiation, evidenced by the enhanced neurite outgrowth, axonal lengths and initiation of neuronal networking (FIG. 4 A-H). Composite collagen substrates with laminin and/or heparan sulfate all maintained a low level of glial fibrillary acidic protein (GFAP) positive glial cells, with initiation of astrocytic networking becoming more obvious at the later time point. In general, substrates that supported neuronal differentiation demonstrated a bare minimum of glial cells required to possibly support neuronal cell phenotype or survival.

Taken together, these results help identify optimal 3D matrix compositions to encapsulate neuronal progenitor cells. In certain embodiments, three dimensional hydrogel environments can also provide the mechanical cues for neural differentiation.

For example, in some embodiments, three dimensional ECM hydrogels can comprise: collagen I (about 800 µg/ml to about 1600 µg/ml); collagen I (about 800 µg/ml) and collagen IV (about 200 µg/ml); collagen I and collagen IV with laminin (about 5 µg/ml to about 10 µg/ml); collagen I and collagen IV with laminin and heparan sulfate (about 10 µg/ml to about 20 µg/ml); Other components of the gel can include: at least 1% fetal calf serum and at least 0.1× antibiotics in Dulbecco's modified Eagle's medium. Sodium hydroxide (0.1N) can be used to adjust pH to about 7.4 for gelation.

Accordingly, methods and systems for treating neurodegenerative conditions are disclosed whereby neural stem cells (NSCs) can be transplanted into a subject in need such that the cells can differentiate and ameliorate the neurodegenerative condition. In certain embodiments, the neural stem cells, upon transplantation, generate an amount of neurons or glial cells sufficient to integrate within the neural infrastructure to ameliorate a disease state or condition. In one embodiment, the disclosed methods include treating neurodegenerative diseases or conditions by transplanting multipotential neural progenitors or neural stem cells isolated from the central nervous system of a mammal and that have been expanded in vitro and induced to differentiate by exposure to at least one component of an extracellular matrix material (ECM).

In another aspect of the invention, treatments can include supplying a suitable number of NSCs to an injured neural area, via transplantation, such that the transplanted cells differentiate into a sufficient number of neurons and/or glial cells to rehabilitate defective neural circuits. In an embodiment, the disclosed methods include restoring motor function in a motor neuron disease. A suitable number or a therapeutically effective amount of NSCs or neural progenitors which are capable of differentiating into motor neurons can be provided to at least one area of neurodegeneration. The NSCs can exert their therapeutic effect by replacing degenerated neuromuscular junctions.

In certain embodiments, the disclosed methods and systems include providing neural stem cells or neural progenitors that integrate with the host tissue and provide one or more factors to the host neurons thereby protecting them from degenerative influences present in the tissue. In one preferred embodiment, the disclosed methods include increasing differentiation efficiency of transplanted NSCs into neurons or glial cells by exposure of the stem cells to one or more extracellular matrix materials (ECMs). The method can also include expanding highly enriched NSCs or neural progenitors in their undifferentiated state and then inducing differentiation so that, upon transplantation, a sufficient number of the cells in the graft adopt a desired phenotype.

The cells of the disclosed methods can be isolated or obtained from fetal, neonatal, juvenile, adult, or post-mortem tissues of a mammal. The cells of the disclosed methods can be isolated or obtained from the central nervous system, blood, or any other suitable source of stem cells that differentiate into neurons. The cells can also be obtained from embryonic stem cells. In certain preferred embodiments, the cells are autologous neural stem cells obtained from a subject and that returned to the subject to ameliorate a neural disorder. In certain embodiments, the neural stem cells can be expanded in culture. In some embodiments, the neural precursor cells can be multipotential NSCs capable of expansion in culture and of generating both neurons and glia upon differentiation.

The cells can be either undifferentiated, pre-differentiated or fully differentiated in vitro at the time of transplantation. In an embodiment, the cells are induced to differentiate into neural lineage. The cells of the disclosed methods can undergo neuronal differentiation in situ in the presence of EMCs and/or pro-inflammatory cytokines and other environmental factors existing in an injured tissue.

Using the present methods, neural circuits can be treated by transplanting or introducing the cells into appropriate regions for amelioration of the disease, disorder, or condition. Generally, transplantation occurs into nervous tissue or non-neural tissues that support survival of the grafted cells. NSC grafts employed in the disclosed methods survive well in a neurodegenerative environment where the NSCs can exert powerful clinical effects in the form of delaying the onset and progression of neurodegenerative conditions or disease.

The present invention can be used in conjunction with various other tissue engineering methods and compositions including those disclosed in commonly-owned, co-pending Applications No. PCT/US2013/024080 entitled "Innervation of Engineered Structures" filed Jan. 31, 2013 and No. PCT/US2013/024024 entitled "Tubular Bioengineered Muscle Structures" also filed Jan. 31, 2013, each of which is incorporated herein in its entirety by reference.

BRIEF DESCRIPTION OF THE DRAWINGS

—FIG. 1A is a phase contrast micrograph of rabbit enteric neurospheres in culture. Upon primary isolation and culture, progenitor cells proliferated and aggregated to form neurosphere-like bodies (enteric neurospheres). Immunohistochemistry for initial phenotype (FIGS. 1 B-D): Rabbit enteric neurospheres are p75NTR (FIG. 1B), Sox2 (FIG. 1C) and Nestin (FIG. 1D) positive—indicating that they are comprised of neural crest-derived neuronal and glial progenitor cells. Scale bar 100 um.

E-H) coverslips coated with PLL (Figs. A,E), laminin (Figs. B,F), type I collagen (Figs. C,G) and type IV collagen (Figs. D,H). Enteric neurospheres on PLL barely initiated neuronal differentiation at day 15. Neurospheres on laminin, collagen I and collagen IV showed branching and several neuronal processes both at the early and late time points in vitro.

Figure 4:
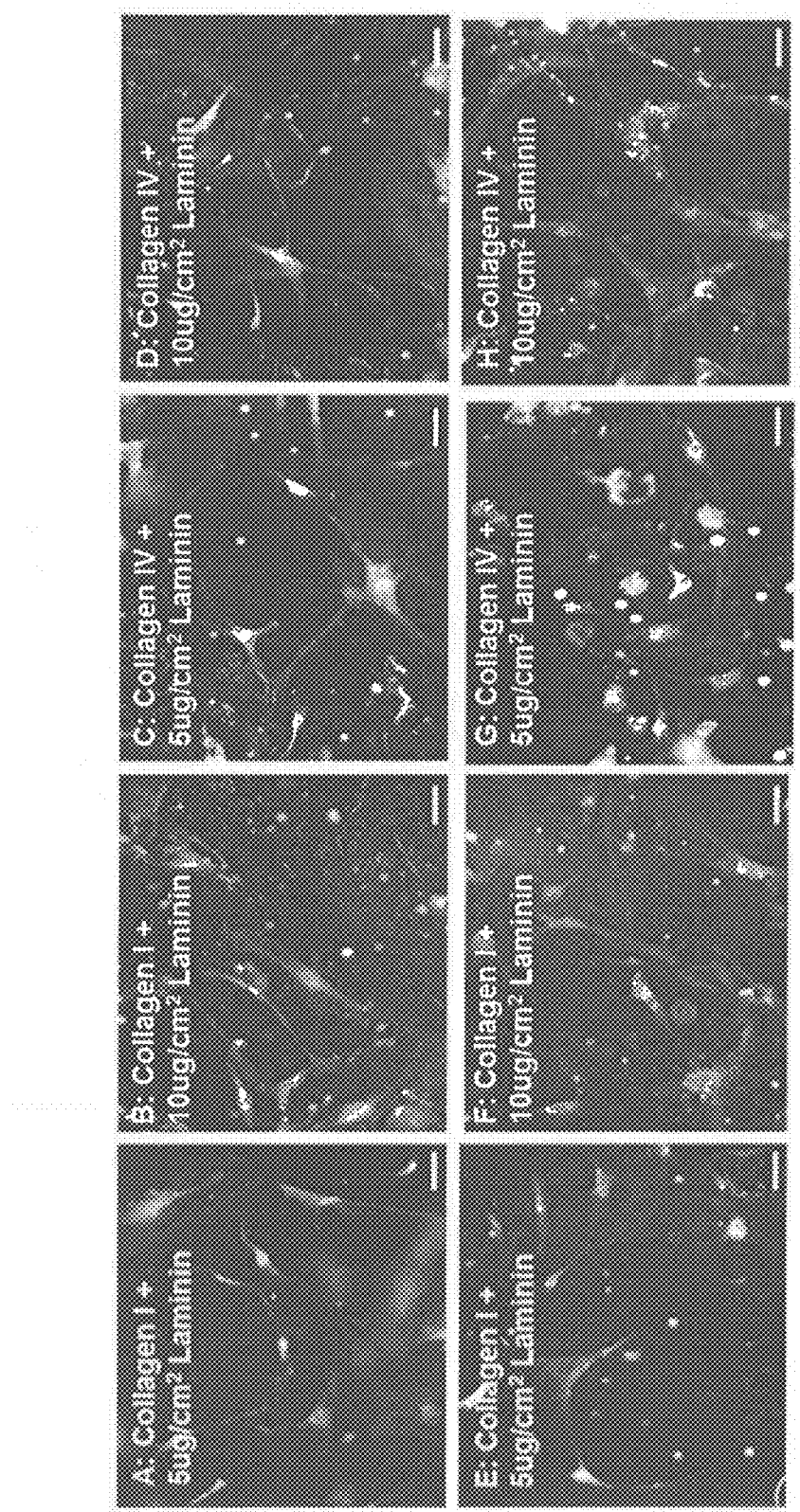

FIG. 4 illustrates neuronal differentiation on collagen-laminin substrates—Neurons stained with βIII tubulin (white) on day 5 (Figs. A-D) and day 15 (Figs. E-H) coverslips coated with type I collagen and 5 μm/cm$^2$ laminin (Figs. A,E) or 10 μm/cm$^2$ laminin (Figs. B,F) or type IV collagen with 5 (Figs. C,G) or 10 (Figs. D,H) μm/cm$^2$ of laminin. Addition of laminin to collagen substrates enhanced early and late neuronal differentiation, but no significant difference was observable between 5 and 10 μg/cm$^2$ of laminin. Type IV collagen substrates (Figs. C,D,G,H) demonstrated enhanced neuronal branching and differentiation compared to type I collagen (Figs. A,B,E,F) substrates.

Figure 5:
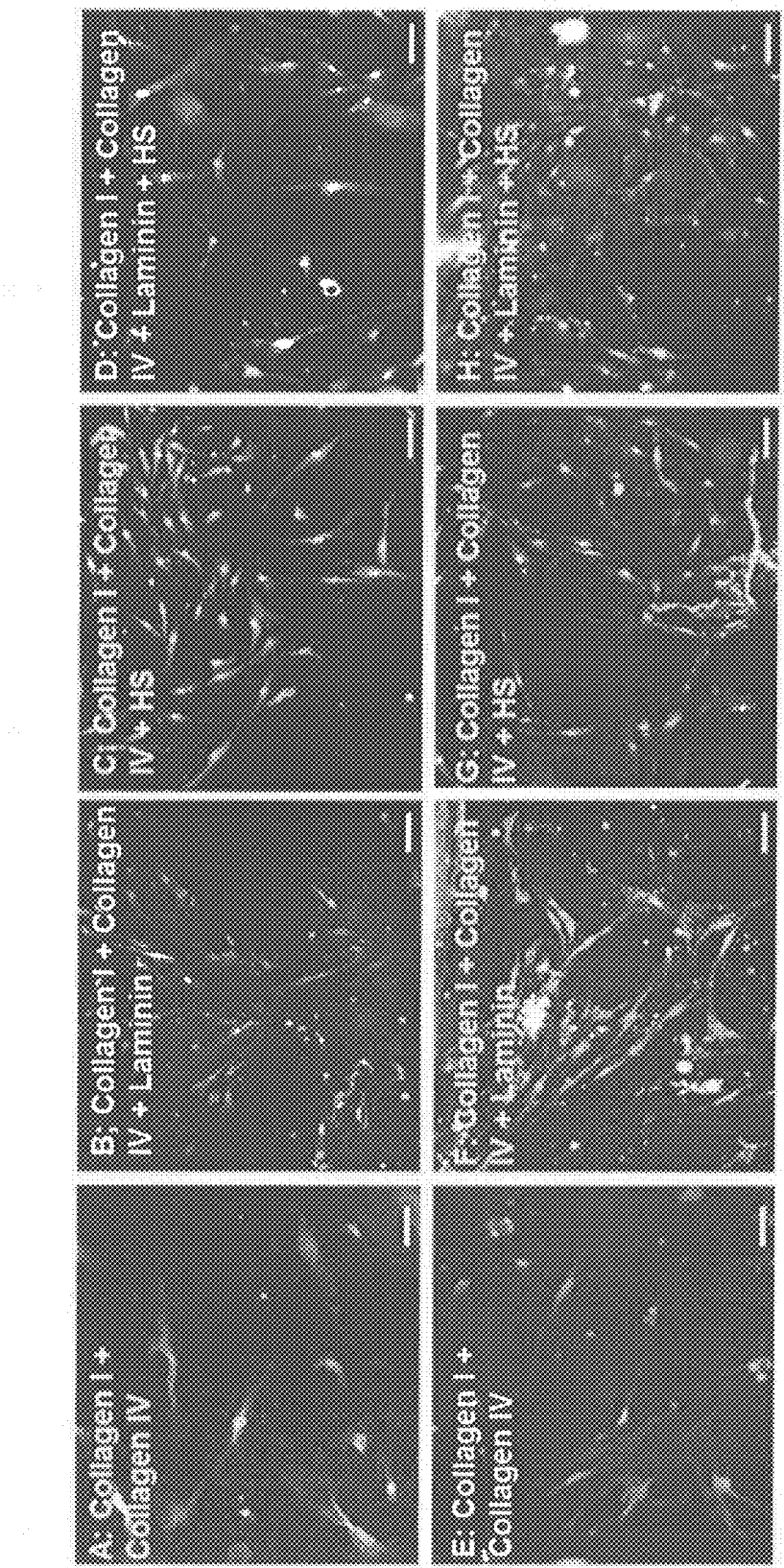

FIG. 5 illustrates neuronal differentiation on composite collagen-laminin-heparan sulfate (HS) substrates—Neurons stained with βIII tubulin (white) on day 5 (Figs. A-D) and day 15 (Figs. E-H) coverslips coated with type I and IV collagen with either 5 μm/cm$^2$ laminin (Figs. B,F), 0.1 μm/cm$^2$ heparan sulfate (HS) (Figs. C,G), both (Figs. D,H) or none (Figs. A,E). Addition of laminin or HS to collagen substrates enhanced early and late neuronal differentiation, with visible networking by day 15. Substrates without laminin or HS demonstrated minimal neuronal differentiation (Figs. A,E).

Figure 6:
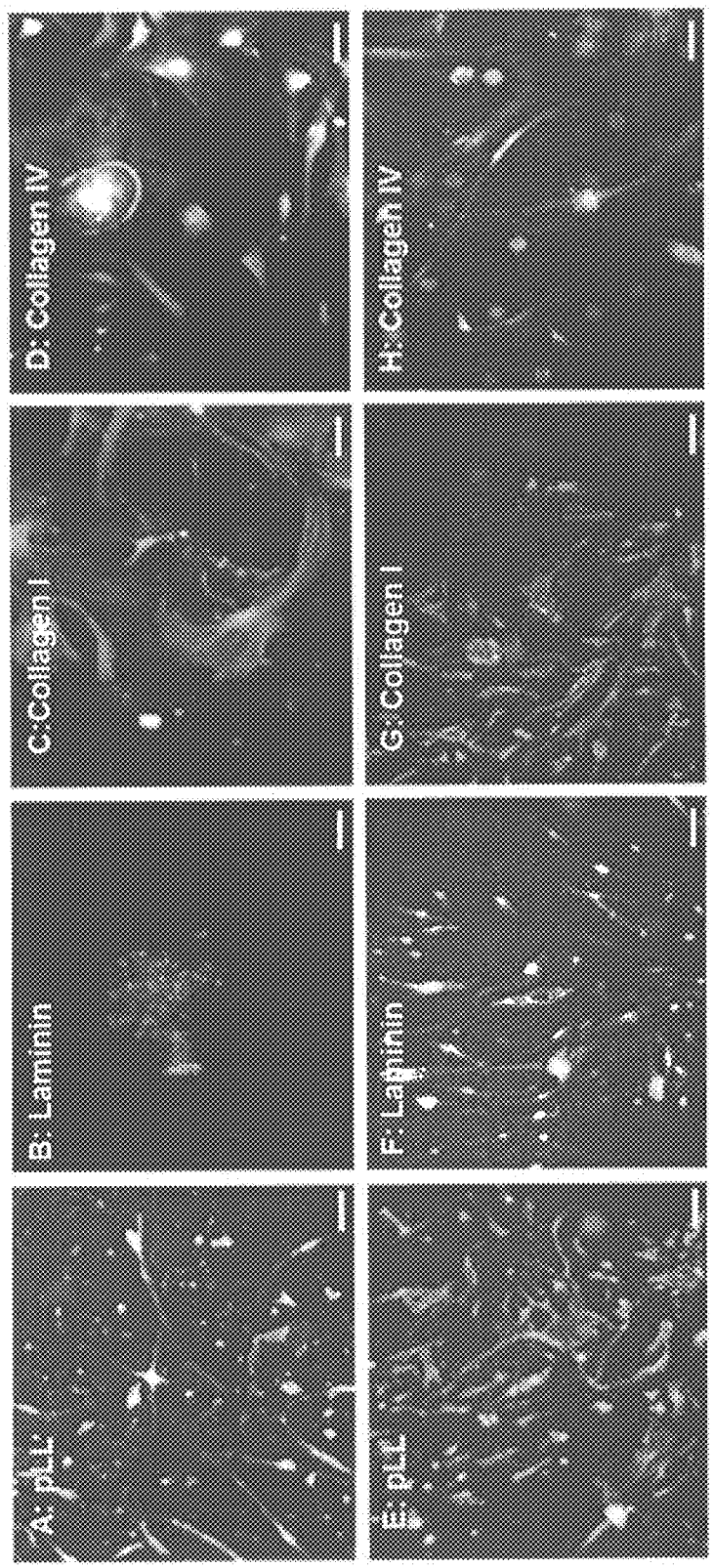

FIG. 6 illustrates glial differentiation on primary coated substrates—Glia stained with GFAP (white) on day 5 (Figs. A-D) and day 15 (Figs. E-H) coverslips coated with poly-L-lysine (PLL) (Figs. A,E), laminin (Figs. B,F), type I collagen (Figs. C,G) and type IV collagen (Figs. D,H). Enteric neurospheres on PLL demonstrated maximal glial differentiation starting at day 5 up to day 15. While neurospheres on collagen substrates demonstrated good early and late glial differentiation, laminin coated substrates showed no early glial differentiation by day 5 (B), but differentiated subsequently by day 15 (F).

Figure 7:
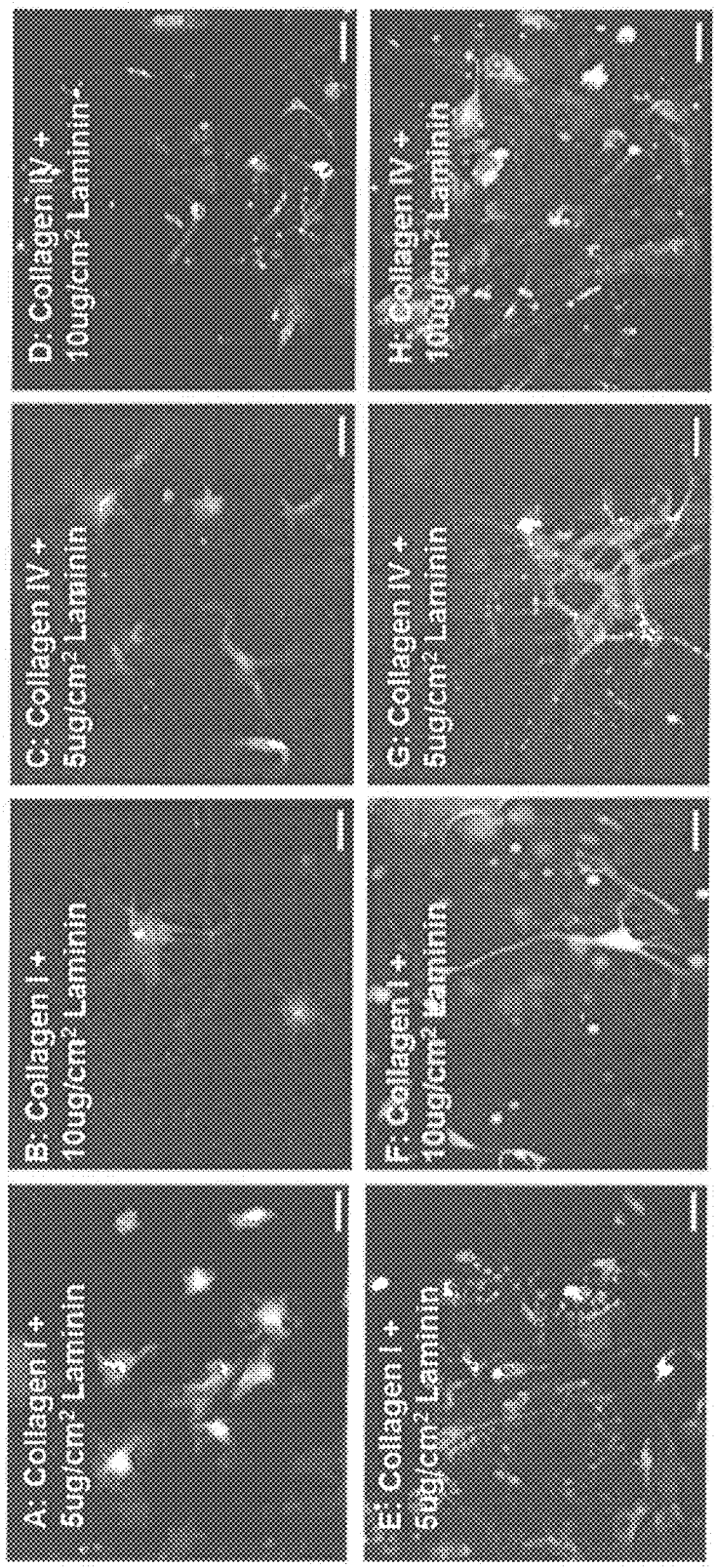

FIG. 7 illustrates glial differentiation on collagen-laminin substrates—Glia stained with glial fibrillary acidic protein (GFAP) (white) on day 5 (Figs. A-D) and day 15 (Figs. E-H) coverslips coated with type I collagen and 5 μg/cm$^2$ laminin (Figs. A,E) or 10 μm/cm$^2$ laminin (Figs. B,F) or type IV collagen with 5 (Figs. C,G) or 10 (Figs. D,H) μm/cm$^2$ of laminin. Addition of laminin to collagen substrates promoted glial differentiation both at days 5 and 15. No significant difference was observable in GFAP+ glial differentiation between 5 and 10 μg/cm$^2$ of laminin.

Figure 8:
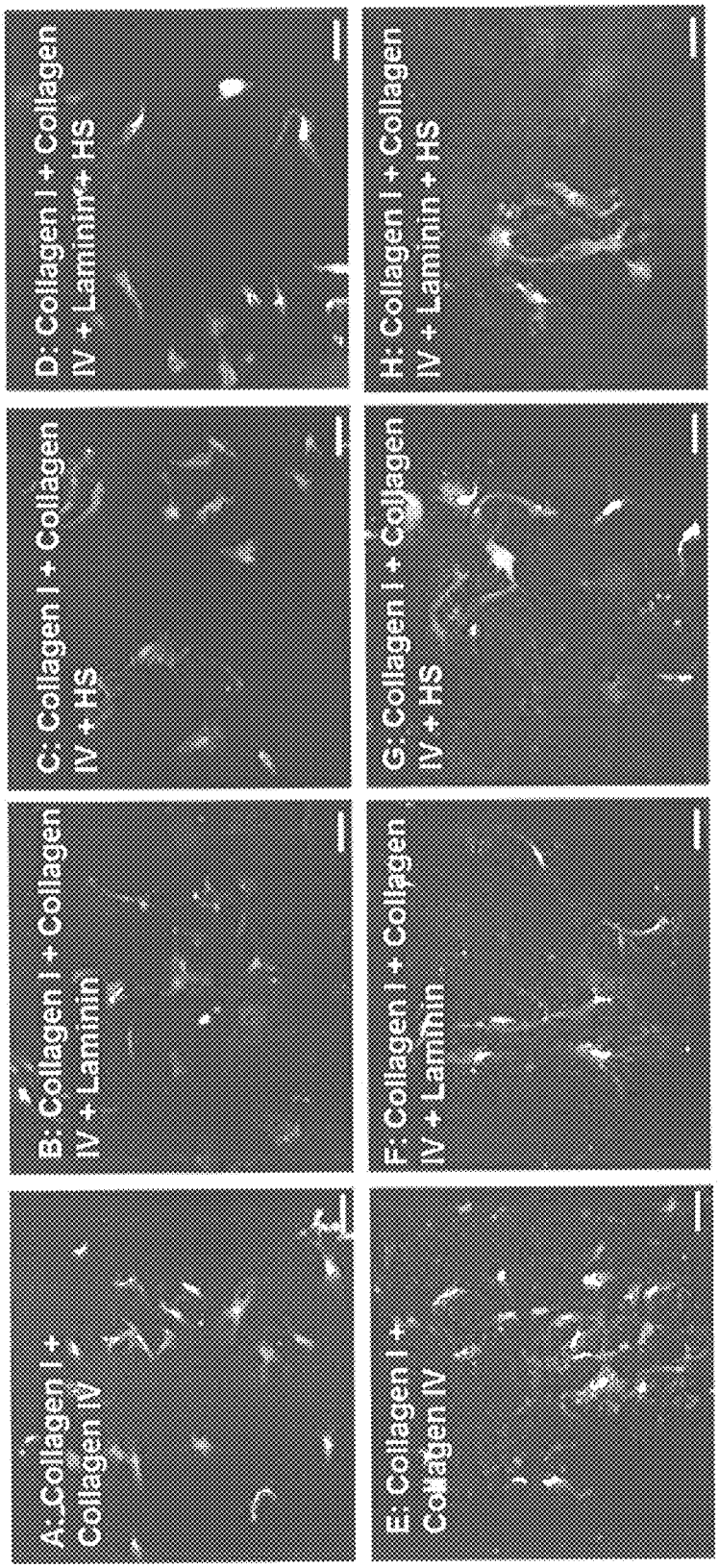
Figure 9:
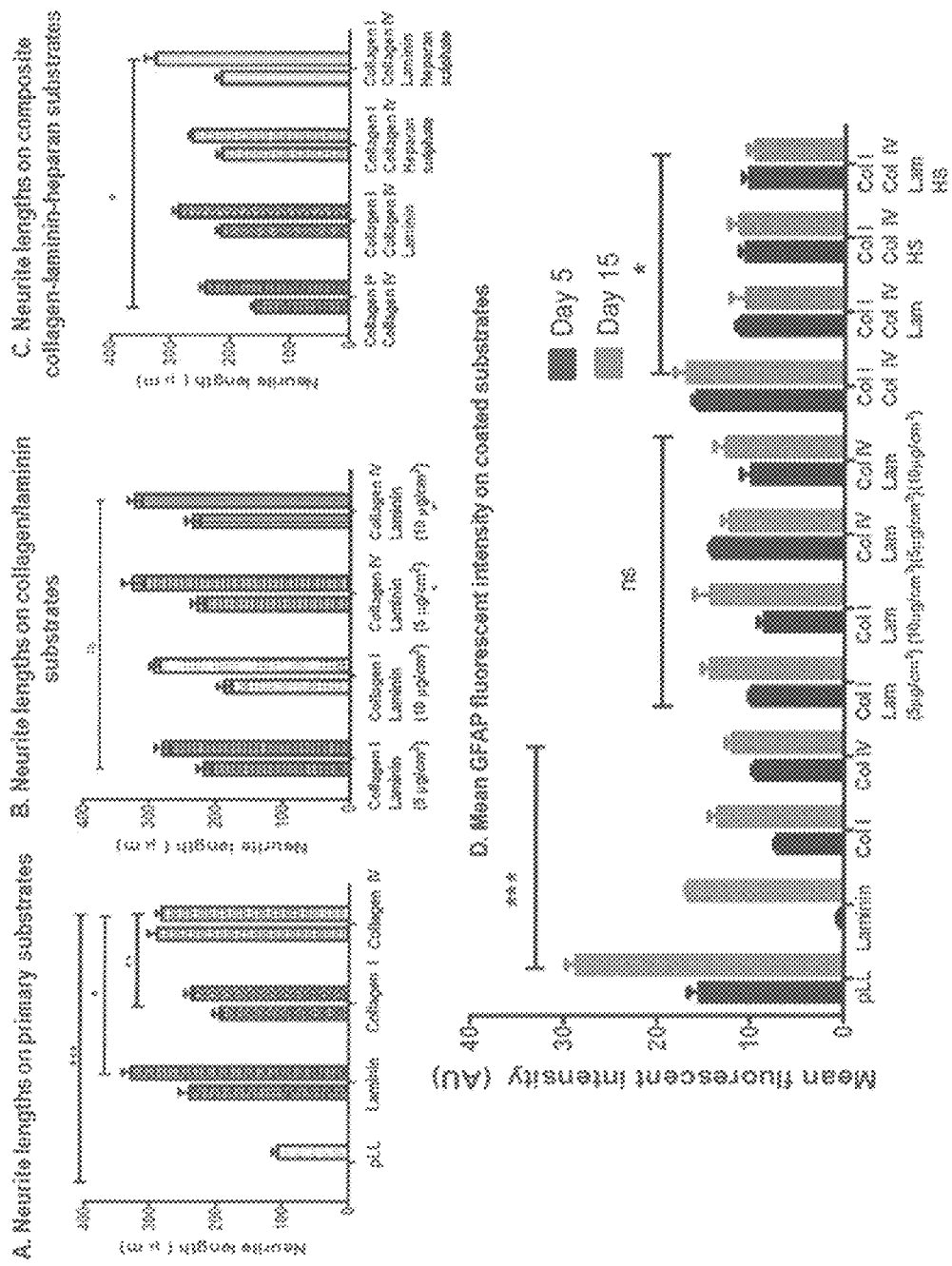

FIG. 8 illustrates glial differentiation on composite collagen-laminin-heparan sulfate (HS) substrates—Glia stained with GFAP (white) on day 5 (Figs. A-D) and day 15 (Figs. E-H) coverslips coated with type I and IV collagen with either 5 μg/cm$^2$ laminin (Figs. B,F), 0.1 μm/cm$^2$ heparan sulfate (Figs. C,G), both (Figs. D,H) or none (Figs. A,E). Addition of laminin or HS to composite collagen substrates demonstrated glial differentiation that peaked at day 5 (Figs. B-D) that was sustained at the later time point (Figs. E-H); and FIG. 9 illustrates neurite lengths were measured on coated culture substrata and compared using one way ANOVA. Two bars for each substrate show mean neurite lengths at day 5 and day 15. FIG. 9A shows that neurite lengths on PLL were significantly (***$p<0.001$) shorter than any primary coating substrate. Laminin substrates had the longer neurites (*$p<0.05$). FIG. 9B shows no significant difference was observed in neurite lengths with the addition of 5 or 10 μg/cm$^2$ laminin. FIG. 9C shows that the addition of laminin or heparan sulphate significantly increased neurite lengths over composite collagen substrata (*$p<0.05$). FIG. 9D shows that mean GFAP immunofluorescence was quantified: PLL substrates (***$p<0.001$) and composite collagen substrates (*$p<0.05$) supported extensive glial differentiation.

Figure 10:
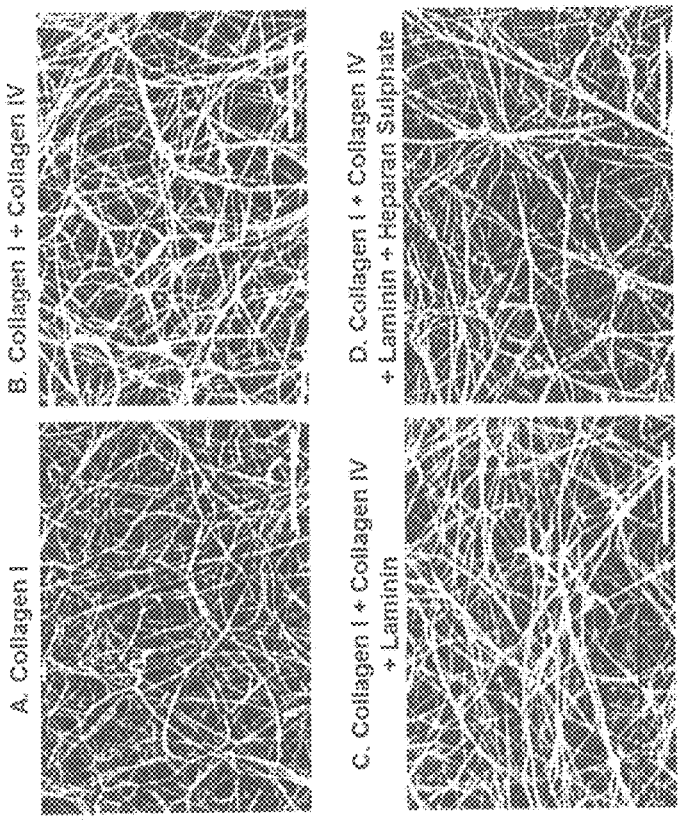

FIG. 10 illustrates scanning electron micrographs of dehydrated ECM gels. Images were obtained at constant magnification and constant working distance. (A) Collagen I fibers were randomly oriented, and presented a dense fibrous structure; (B) Composite Collagen I/IV sheets demonstrated evidence of the formation of network-like structures; (C) There was no difference in ultrastructure with the addition of laminin; (D) Evidence of cabling and cross-linking was observed with the addition of heparan sulfate. Average porosity was determined and summarized in the accompanying table. Viscoelastic modulus was calculated using oscillatory rheometry of ECM gels in their hydrated state, and tabulated in the table. Scale bar 10 μm.

Figure 11:
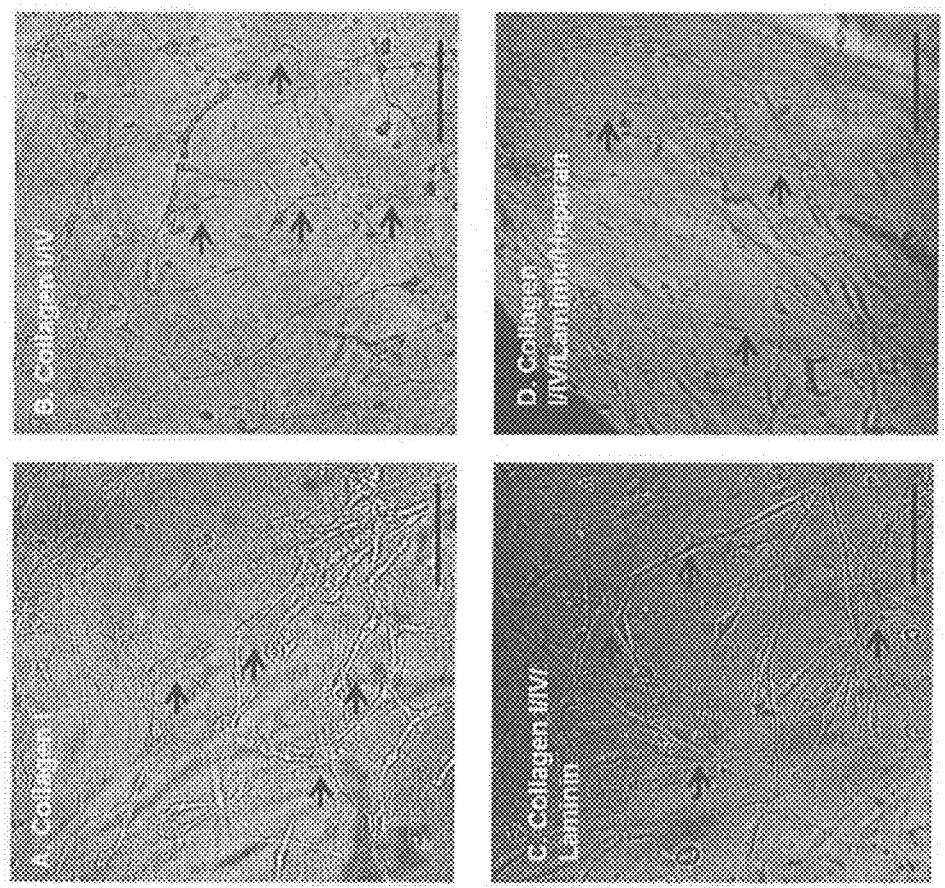

FIG. 11 illustrates neuronal differentiation within tissue engineered sheets. Phase contrast micrographs were obtained at the edge of the tissue engineered sheets. Evidence of neuronal differentiation and initiation of network formation was observed in all ECM compositions at day 10. The arrows indicate instances of preliminary neuronal networking. Scale bar 200 μm.

Figure 12:
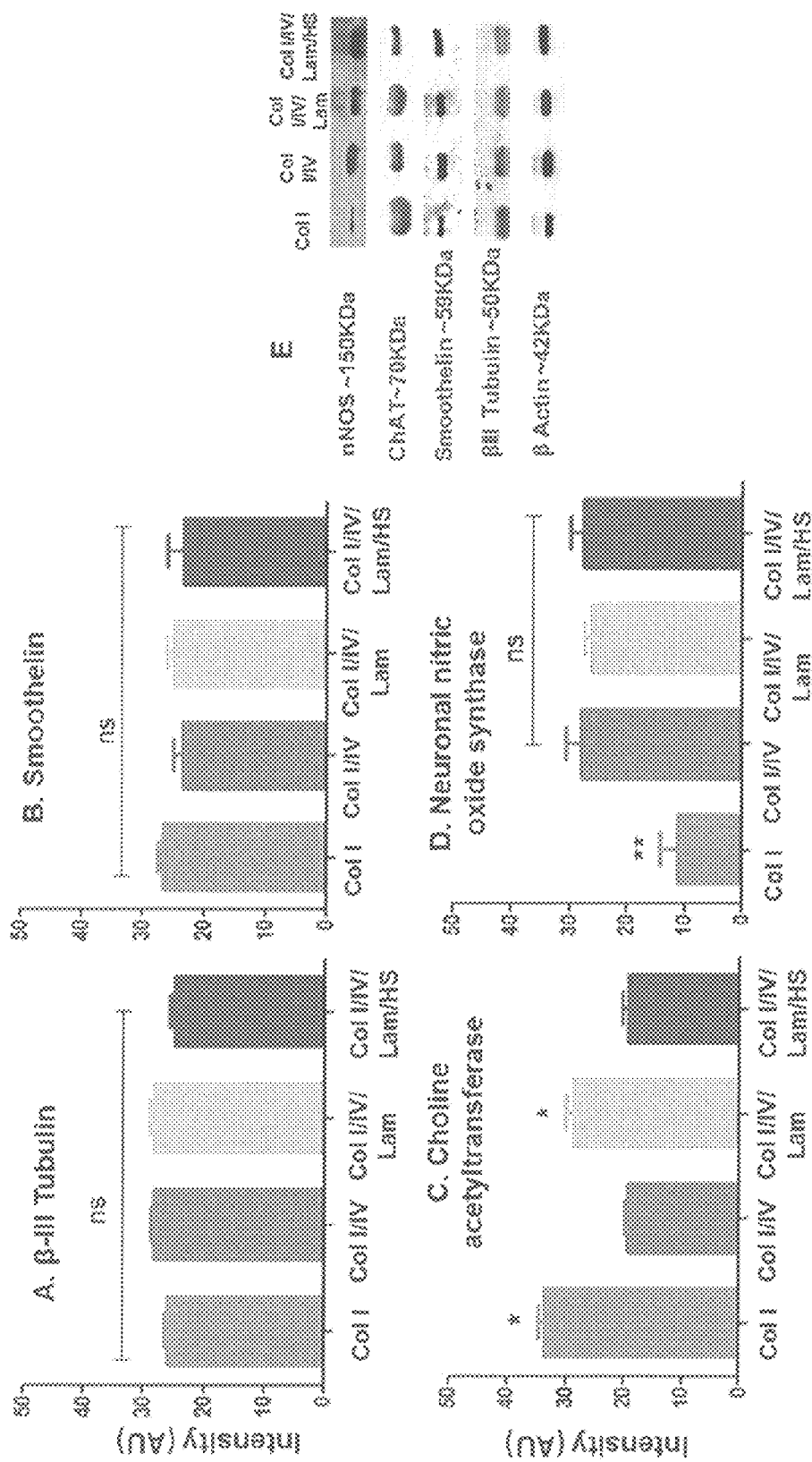

FIG. 12 illustrates immunoblot analysis of tissue engineered longitudinal sheets. Sheets were assessed for expression of neuronal differentiation, constituent smooth muscle phenotype, and excitatory and inhibitory neural markers. Densitometry was used to quantify band intensities, to quantify and compare expression. (A) Neuronal βIII Tubulin expression was similar amongst all four matrices suggesting that all ECM compositions supported neuronal differentiation; (B) Constituent smooth muscle within the tissue engineered sheets maintained contractile phenotype, demonstrated by similar Smoothelin expression; (C) Choline acetyltransferase (ChAT) expression was significantly (*$p<0.05$) elevated in Col I and Col I/IV/Laminin sheets compared to Col I/IV and Col I/IV/Lam/HS sheets; (D) Neuronal nitric oxide synthase (nNOS) expression was significantly lower (**$p<0.001$) in Col I sheets compared to elevated levels in all tissue engineered sheets containing Col4 with or without laminin and/or heparan sulfate. (E) Representative immunoblots are provided along with β Actin, demonstrating equal loading.

Figure 13:
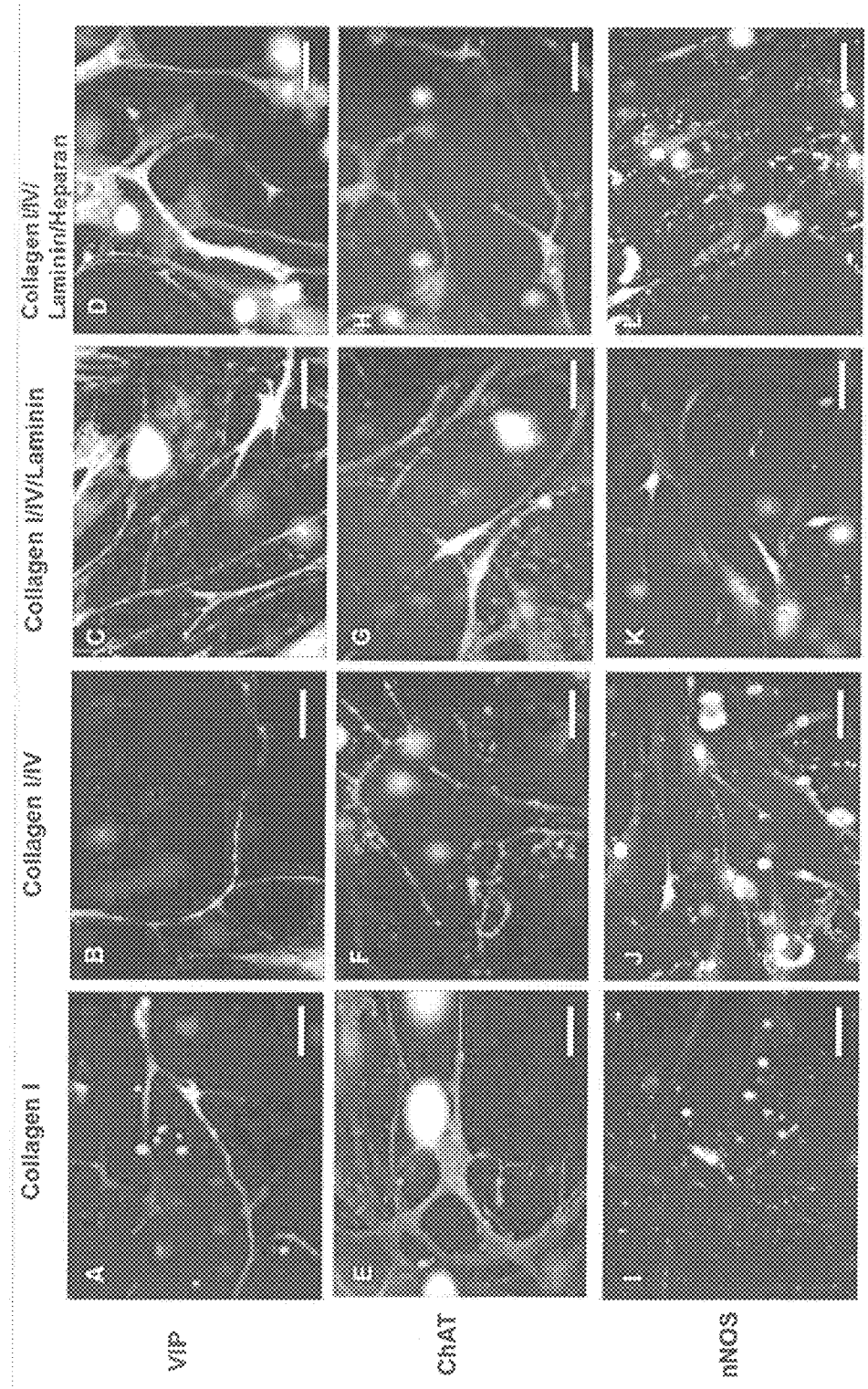

FIG. 13 illustrates immunofluorescence for differentiated neurons within tissue engineered sheets. Differentiated neurons within tissue engineered sheets were stained with markers for vasoactive intestinal peptide (VIP), choline acetyltransferase (ChAT) or neuronal nitric oxide synthase (nNOS). (A-D) Numerous differentiated VIP-ergic neurons were present in tissue engineered sheets. (E-H) Differentiated excitatory cholinergic neurons expressing ChAT were present within tissue engineered sheets; (I-L) Differentiated inhibitory nitrergic neurons expressing nNOS were present within tissue engineered sheets. Scale bar 100 μm.

Figure 14:
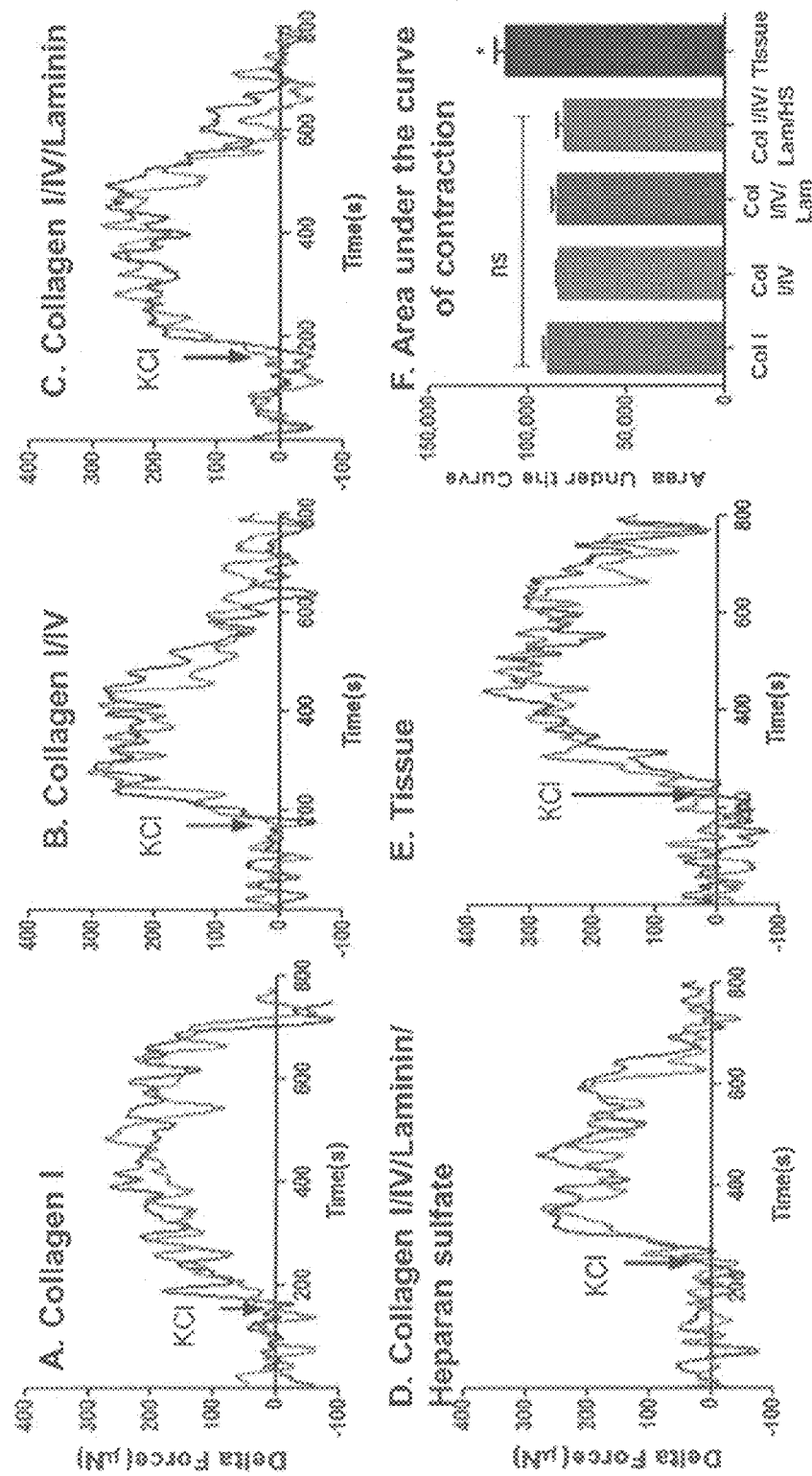

FIG. 14 illustrates potassium chloride induced contraction of tissue engineered sheets. 60 mM Potassium chloride (KCl) was used to examine the electromechanical coupling integrity of the constituent smooth muscle cells within the tissue engineered sheets. The black traces indicate the contraction in response to the addition of KCl. The grey traces indicate the addition of KCl in the presence of a neuronal blocker, TTX. Pre-treatment with TTX did not inhibit KCl-induced contraction. The ECM composition of the tissue engineered sheets did not affect smooth muscle contraction, evidenced by similar contractile patterns in response to KCl stimulation. A robust and immediate contraction was observed upon addition of KCl (indicated by the arrows) in all tissue engineered sheets (A-D), similar to native rabbit intestinal tissue (E). Peak contraction in response to KCl ranged between 279.5 µN and 296.5 µN in tissue engineered sheets, and averaged at 373.3±10.63 in native tissue. (F) The area under the curve of KCl-induced contraction was quantified to demonstrate no significant (ns) difference in contraction in tissue engineered sheets, with a slightly elevated (*p<0.05) magnitude in native tissue.

Figure 15:
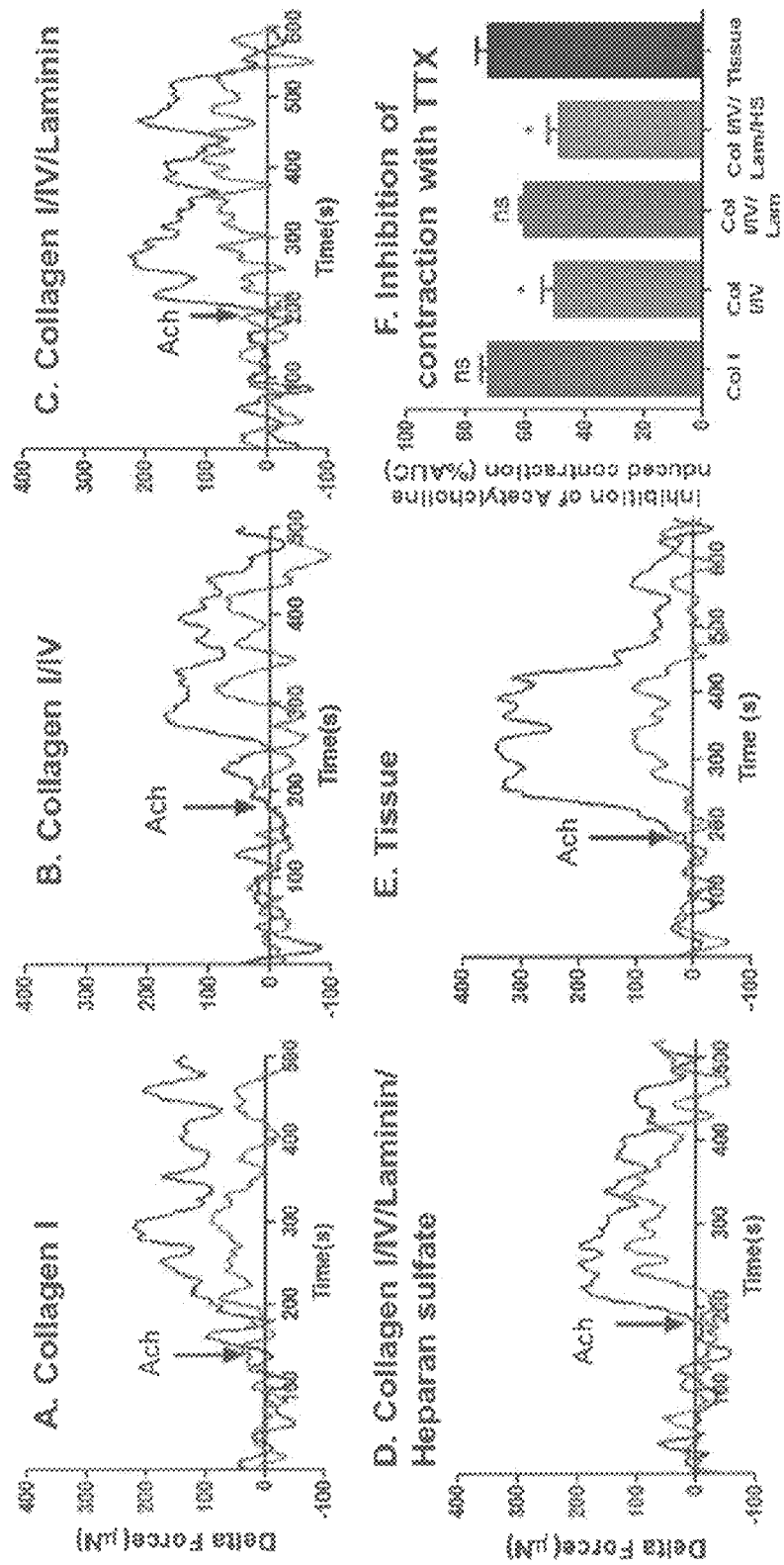

FIG. 15 illustrates acetylcholine induced contraction. Addition of 1 µM Acetylcholine (Ach; arrow) resulted in contraction of tissue engineered sheets, as well as native tissue. Gray traces demonstrate Ach treatment in the presence of neuronal blocker, TTX. (A-E) Representative tracings of Ach-induced contraction in tissue engineered sheets and native tissue. Magnitude of Ach-induced contraction varied between tissue engineered sheets. Comparison of the area under the curve of contraction demonstrated that tissue engineered sheets approached 31.5% (Col4)-67.6% (Laminin) of contraction observed in native tissue. In the presence of TTX, magnitude of Ach-induced contraction was attenuated. Quantification of inhibition (F) revealed that the degree of inhibition with TTX varied amongst the tissue engineered sheets with different ECM compositions. Highest inhibition was observed in Col i (72.77±2.5%) and Col I/IV/Laminin (60.58±1.7%) sheets, indicating an elevated presence of cholinergic neurons contributing to Ach-induced contraction. Significantly lower inhibition (*p<0.05; 48.36±4.3-50.31±4.2%) was seen in Col I/IV and Col I/IV/Lam/Heparan sulfate sheets. TTX pre-treatment attenuated Ach-induced contraction by 72.73±3.7% in native tissue.

Figure 16:
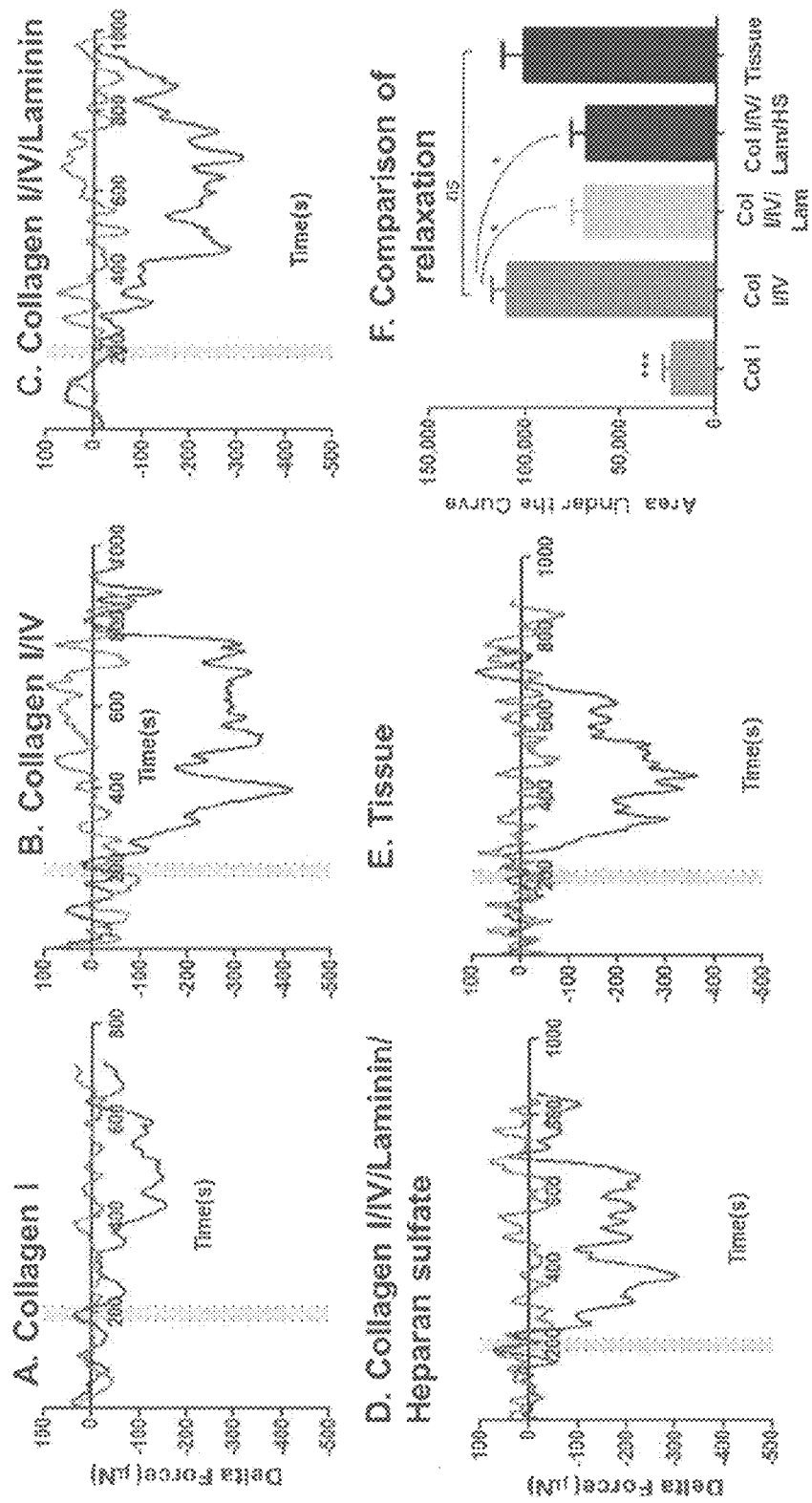

FIG. 16 illustrates electrical Field Stimulation induced relaxation in tissue engineered sheets. Electrical Field stimulation (EFS; shaded gray area) was used to stimulate relaxation in tissue engineered sheets (A-D) and native tissue (E). Grey traces indicate TTX pre-treatment. EFS induced relaxation was significantly attenuated by TTX-pretreatment (90.9±2.41%-94.41±0.93%), indicating that differentiated neurons within the tissue engineered sheets were capable of evoking smooth muscle relaxation. The magnitude of relaxation varied amongst the tissue engineered sheets (summarized in Table 3). (F) Quantification of the area under the curve of relaxation indicated that Col I sheets had a significantly low (***p<0.001; 23142±4921 AU) magnitude of relaxation. Relaxation in Col I/IV sheets (109693±8465 AU) were similar to those observed in native tissue (101550±11279 AU) in response to the electrical field, indicating the presence of elevated levels of inhibitory motor neurons capable of mediating relaxation. Relaxation was higher in Col I/IV/Laminin (69025±7154 AU) and Col I/IV/Lam/Heparan sulfate (68395±8228 AU) sheets, when compared to Col I, also indicating a similar increase in the presence of inhibitory motor neurons.

Figure 17:
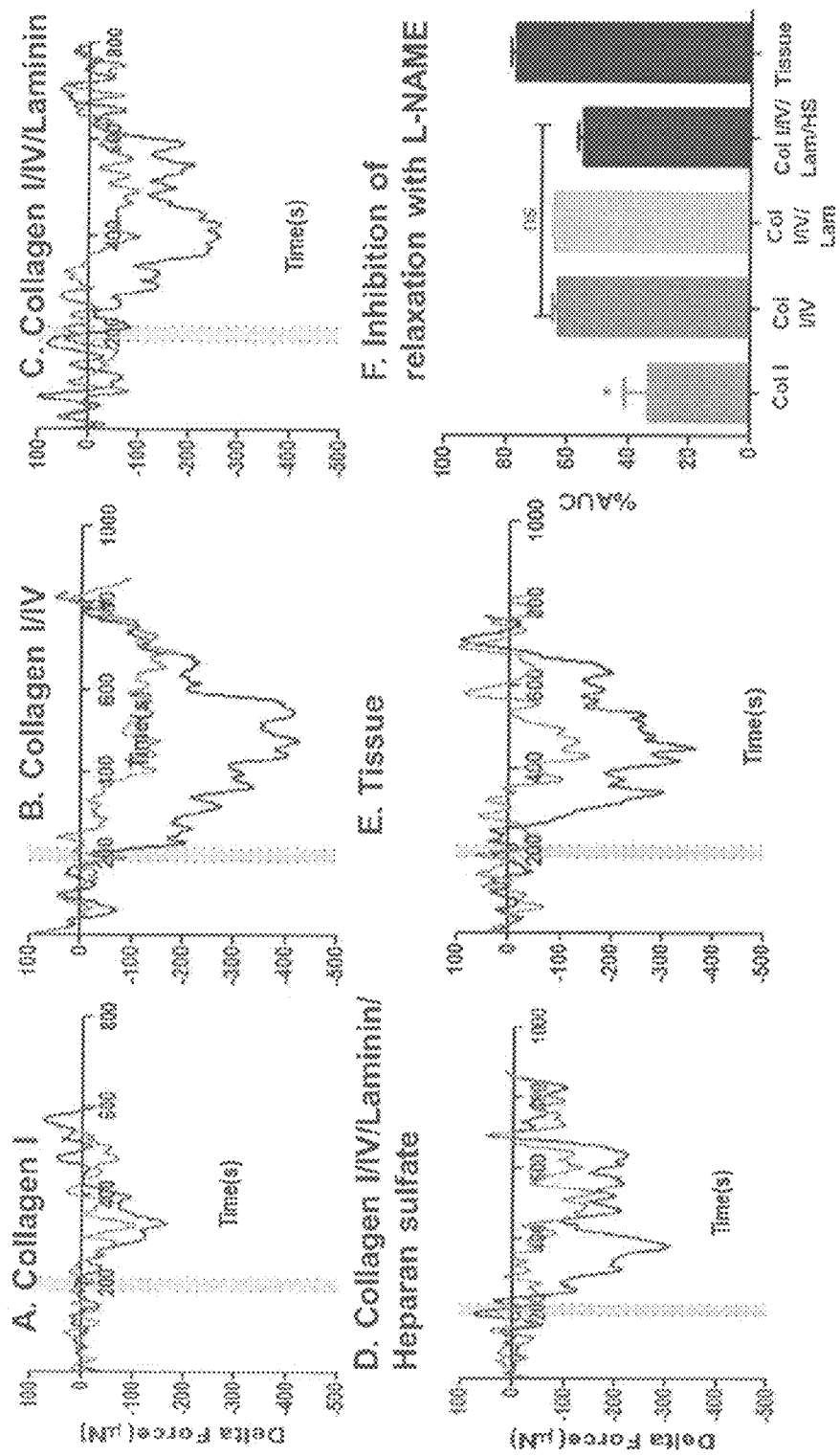

FIG. 17 illustrates inhibition of relaxation with L-NAME. The functionality of nitrergic neurons was studied by inhibiting EFS-induced relaxation with L-NAME, a non-metabolizable substrate for nNOS. The grey traces indicate EFS in the presence of L-NAME. Pretreatment with L-NAME attenuated EFS-induced relaxation in all tissue engineered sheets (A-D) and native tissue (E). (F) Quantification of the area under the curve for relaxation indicated that the extent of L-NAME inhibition varied amongst the tissue engineered sheets. Col I sheets had a significantly lower % inhibition with L-NAME (*p<0.05; 33.4±8.4%) corresponding to the lowest immunoblot expression of nNOS. The degree of L-NAME inhibition was higher in tissue engineered sheets containing Col I/IV and/or laminin and/or heparan sulfate (57.16%-62.28%), corresponding to the higher immunoblot expression of nNOS. Attenuation of relaxation in the presence of L-NAME was 78±2.9% in native tissue.

Figure 18:
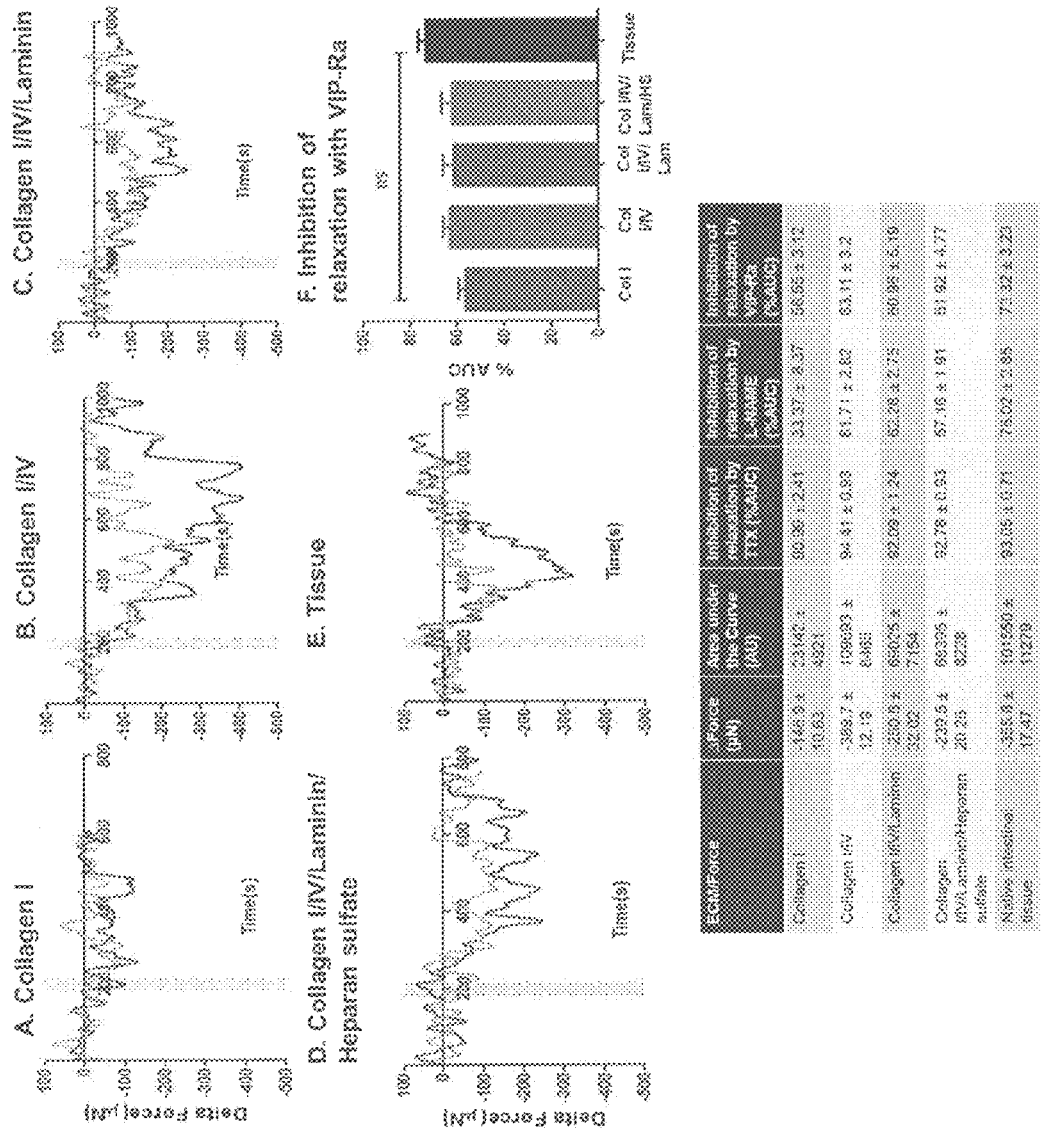

FIG. 18 illustrates inhibition of relaxation with VIP-Ra. The functionality of VIP-ergic neurons was studied by inhibiting EFS-induced relaxation with VIP-Ra, a VIP-receptor antagonist. Grey traces indicate EFS in the presence of VIP-Ra. In the presence of VIP-Ra, EFS-induced relaxation was attenuated in tissue engineered sheets (A-D) and in native tissue (E), indicating the presence of functional VIP-ergic neurons capable of mediating smooth muscle relaxation upon electrical field stimulation. Area under the curve of relaxation was quantified, to calculate the % inhibition of relaxation in the presence of VIP-Ra (F). Extent of VIP-Ra induced inhibition of relaxation varied from 56.55±3.12%-63.11±3.2% in tissue engineered sheets, and averaged at 73.32±3.23% in native tissue.

DETAILED DESCRIPTION

Definitions

As used in this specification and the appended claims, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth. The steps of any method can be practice in feasible order and are restricted to a sequential order merely because they are so recited in a claim.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

"Differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

Stem cells are undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts. Neural stem cells can be isolated from embryonic and adult central nervous system (CNS) tissue, neural tube tissue or enteric nervous system (ENS) tissue.

Stem cells can be further classified according to their developmental potential as: (1) totipotent; (2) pluripotent; (3) multipotent; (4) oligopotent; and (5) unipotent. Totipotent cells are able to give rise to all embryonic and extra-embryonic cell types. Pluripotent cells are able to give rise to all embryonic cell types. Multipotent cells include those able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood). Cells that are oligopotent can give rise to a more restricted subset of cell lineages than multipotent stem cells; and cells that are unipotent typically are only able to give rise to a single cell lineage.

In a broader sense, a progenitor cell is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase "differentiates into a neural lineage or phenotype" refers to a cell that becomes partially or fully committed to a specific neural phenotype of the CNS or PNS, i.e., a neuron or a glial cell, the latter category including without limitation astrocytes, oligodendrocytes, Schwann cells and microglia. The term "neural" as used herein is intended to encompass all electrical active cells, e.g., cells that can process or transmit information through electrical or chemical signals, including the aforementioned neurons, glial cells, astrocytes, oligodendrocytes, Schwann cells and microglia.

For the purposes of this disclosure, the terms "neural progenitor cell" or "neural precursor cell" mean a cell that can generate progeny that are either neuronal cells (such as neuronal precursors or mature neurons) or glial cells (such as glial precursors, mature astrocytes, or mature oligodendrocytes). Typically, the cells express some of the phenotypic markers that are characteristic of the neural lineage. Typically, they do not produce progeny of other embryonic germ layers when cultured by themselves in vitro, unless dedifferentiated or reprogrammed in some fashion.

A "neuronal progenitor cell" or "neuronal precursor cell" is a cell that can generate progeny that are mature neurons. These cells may or may not also have the capability to generate glial cells. A "glial progenitor cell" or "glial precursor cell" is a cell that can generate progeny that are mature astrocytes or mature oligodendrocytes. These cells may or may not also have the capability to generate neuronal cells.

The phrase "biocompatible substance" and the terms "biomaterial" and "substrate" are used interchangeably and refer to a material that is suitable for implantation or injection into a subject. A biocompatible substance does not cause toxic or injurious effects once implanted in the subject. In one embodiment, the biocompatible substrate includes at least one component of extracellular matrix. In other embodiments, the substrate can also include a polymer with a surface that can be shaped into the desired structure that requires repairing or replacing. The polymer can also be shaped into a part of a body structure that requires repairing or replacing. In another embodiment, the biocompatible substrate can be injected into a subject at a target site.

In one embodiment, the substrate is an injectable or implantable biomaterial that can be composed of crosslinked polymer networks which are typically insoluble or poorly soluble in water, but can swell to an equilibrium size in the presence of excess water. For example, a hydrogel can be injected into desired locations within the organ. In one embodiment, the collagen can be injected alone. In another embodiment, the collagen can be injected with other hydrogels. The hydrogel compositions can include, without limitation, for example, poly(esters), poly(hydroxy acids), poly(lactones), poly(amides), poly(ester-amides), poly(amino acids), poly(anhydrides), poly(ortho-esters), poly(carbonates), poly(phosphazines), poly(thioesters), polysaccharides and mixtures thereof. Furthermore, the compositions can also include, for example, a poly(hydroxy) acid including poly(alpha-hydroxy) acids and poly(beta-hydroxy) acids. Such poly(hydroxy) acids include, for example, polylactic acid, polyglycolic acid, polycaproic acid, polybutyric acid, polyvaleric acid, and copolymers and mixtures thereof.

Hydrogels with effective pore sizes in the 10-100 nm range and in the 100 nm-10 micrometer range are termed "microporous" and "macroporous" hydrogels, respectively. Microporous and macroporous hydrogels are often called polymer "sponges." When a monomer, e.g., hydroxyethyl methacrylate (HEMA), is polymerized at an initial monomer concentration of 45 (w/w) % or higher in water, a hydrogel is produced with a porosity higher than the homogeneous hydrogels. Hydrogels can also expand in the presence of diluent (usually water). The matrix materials of present invention encompass both conventional foam or sponge materials and the so-called "hydrogel sponges." For a further description of hydrogels, see U.S. Pat. No. 5,451,613 (issued to Smith et al.) herein incorporated by reference.

The term "extracellular matrix" or "ECM" is used herein to denote compositions comprising one or more of the following: collagen I, collagen IV, laminin, heparan sulfate, or fragments of one or more of such proteins.

"Collagen I" refers to collagen I or collagen I compositions derived from cell culture, animal tissue, or recombinant means, and may be derived from human, murine, porcine, or bovine sources. "Collagen I" also refers to substances or polypeptide(s) at least substantially homologous to collagen I or collagen I compositions. Additionally, "collagen I" refers to collagen I or collagen I compositions that do not include a collagen I fragment, e.g., including essentially only a complete collagen I protein.

"Collagen IV" refers to collagen IV or collagen IV compositions derived from cell culture, animal tissue, or recombinant means, and may be derived from human, murine, porcine, or bovine sources. "Collagen IV" also refers to substances or polypeptide(s) at least substantially homologous to collagen IV or collagen IV compositions. Additionally, "collagen IV" refers to collagen IV or collagen IV compositions that do not include a collagen IV fragment, e.g., including essentially only a complete collagen I protein.

"Laminin" refers to laminin, laminin fragments, laminin derivatives, laminin analogs, or laminin compositions derived from cell culture, recombinant means, or animal tissue. "Laminin" can be derived from human, murine, porcine, or bovine sources. "Laminin" refers to laminin or laminin compositions comprising laminin-1, laminin-2, laminin-4, or combinations thereof. "Laminin" also refers to substances or polypeptide(s) at least substantially homologous to laminin-1, laminin-2, or laminin-4. Additionally, "laminin" refers to laminin or laminin compositions that do not include a laminin fragment, e.g., including essentially only a complete laminin protein.

The term "substantially free of laminin" and "free of laminin" are used interchangeably herein to denote compositions in which laminin is absent or present in such low concentrations that it does not play any significant role in neural stem cell differentiation, e.g., where laminin is only present in concentrations less than 5 µg/ml in hydrogels or 5 µg/cm on substrate coatings, or more preferably less than 2 µg/ml in hydrogels or 2 µg/cm$^2$ on substrate coatings, or less than 1 µg/ml in hydrogels or 1 µg/cm on substrate coatings, and in some instances less than 0.1 µm/ml in hydrogels or 0.1 µm/cm$^2$ on substrate coatings.

The term "substantially free of heparan sulfate" and "free of heparan sulfate" are used interchangeably herein to denote compositions in which heparin sulfate is absent or present in such low concentrations that it does not play any significant role in neural stem cell differentiation, e.g., where heparan sulfate is only present in concentrations less than 5 µg/ml in hydrogels or 5 µg/cm$^2$ on substrate coatings, or more preferably less than 2 µg/ml in hydrogels or 2 µg/cm$^2$ on substrate coatings, or less than 1 µg/ml in hydrogels or 1 µg/cm$^2$ on substrate coatings, and in some instances less than 0.1 µm/ml in hydrogels or 0.1 µm/cm$^2$ on substrate coatings.

General Techniques

For further elaboration of general techniques useful in the practice of this invention, the practitioner can refer to standard textbooks and reviews in cell biology, tissue culture, and embryology. Included are Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998), For elaboration of nervous system abnormalities, and the characterization of various types of nerve cells, markers, and related soluble factors, the reader is referred to CNS Regeneration: Basic Science and Clinical Advances, M. H. Tuszynski & J. H. Kordower, eds., Academic Press, 1999.

Methods in molecular genetics and genetic engineering are described in Molecular Cloning: A Laboratory Manual, 2nd Ed. (Sambrook et al., 1989); Oligonucleotide Synthesis (M. J. Gait, ed., 1984); Animal Cell Culture (R. I. Freshney, ed., 1987); the series Methods in Enzymology (Academic Press); Gene Transfer Vectors for Mammalian Cells (J. M. Miller & M. P. Calos, eds., 1987); Current Protocols in Molecular Biology and Short Protocols in Molecular Biology, 3rd Edition (F. M. Ausubel et al., eds., 1987 & 1995); and Recombinant DNA Methodology II (R. Wu ed., Academic Press 1995). Reagents, cloning vectors, and kits for genetic manipulation referred to in this disclosure are available from commercial vendors such as BioRad, Stratagene, Invitrogen, and ClonTech.

General techniques used in raising, purifying and modifying antibodies, and the design and execution of immunoassays including immunohistochemistry are described in Handbook of Experimental Immunology (D. M. Weir & C. C. Blackwell, eds.); Current Protocols in Immunology (J. E. Coligan et al., eds., 1991); and R. Masseyeff, W. H. Albert, and N. A. Staines, eds. Methods of Immunological Analysis (Weinheim: VCH Verlags GmbH, 1993).

Sources of Stem Cells

This invention can be practiced using stem cells of various types, which may include the following non-limiting examples: U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,654,183 and 5,849,553 report the use of mammalian neural crest stem cells. U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors. U.S. Pat. No. 5,968,829 reports neural stem cells obtained from embryonic forebrain and cultured with a medium comprising glucose, transferrin, insulin, selenium, progesterone, and several other growth factors.

Except where otherwise required, the invention can be practiced using stem cells of any vertebrate species. Included are stem cells from humans; as well as non-human primates, domestic animals, livestock, and other non-human mammals.

Neural Glial Differentiation

Enteric neuronal progenitor cells have been identified in the adult mammalian gut, and have been isolated from humans up to and over 80 years of age. Previously, several groups have shown that a self-renewing population of Sox 2, Sox10, Nestin and p75 positive neural-crest derived progenitor cells can be isolated either from full-thickness, muscularis or mucosal biopsies of the adult mammalian gut. These cells have been demonstrated to have the potential to differentiate into several neuronal subtypes including inhibitory and excitatory motor neurons and glia.

Various types of neuronal progenitor cells (CNS-derived, neural tube-derived, embryonic and adult ENS-derived) from explant cultures of aneural gut can also be transplanted. Alterations in the extracellular matrix of the gut mesenchyme has been documented in aganglionic regions of rodent gut, suggesting the importance of a permissive extracellular environment to promote effective in utero colonization and differentiation of neural crest cells in the developing gut. Since transplantation and subsequent functional neo-innervation is one clinical goal of neural stem cell transplantation, in vitro studies should mimic developmental conditions in vivo, in terms of providing a permissive and favorable ECM (such as a three-dimensional environment). Understanding the role of the ECM in affecting neuroglial differentiation of adult enteric neuronal progenitor cells can enhance the survivability and maintenance of a stable phenotype upon transplantation.

Mammalian myenteric ganglia in vivo are surrounded by a matrix comprised predominantly of type IV collagen, laminin, heparan sulphate proteoglycan, and entactin. The enteric plexus lacks large connective tissue spaces for blood vessels like the peripheral nervous system. The two-dimensional culture substratum may modulate neuronal and glial differentiation based on ECM composition. Different ECM components may influence enteric glia and neurons come in to contact with in vivo in the adult myenteric plexus, such as collagen IV, laminin and heparan sulfate.

Addition of laminin to collagen substrates unexpectedly improved neurite outgrowth with longer neurite lengths (compare 156.1±7.2 µm to 215.1±7.6 µm). while there was an overall enhancement in neuronal differentiation as well as neurite outgrowth, there was no significant difference between the additions of 5 or 10 µg/cm$^2$ of laminin. This empirical determination was important in determining a minimal amount of laminin that can influence neuroglial differentiation without affecting neurite outgrowth adversely in a situation that requires neo-innervation of denervated tissues.

Addition of heparan sulfate to composite collagen mixtures improved neuronal differentiation as well. Neuronal networking and neuronal clustering was visible at the later time point. Heparan sulfate may interact with GDNF and other neurotrophic factors to stabilize and make the factors locally available. Heparan sulfate interacts with both collagen IV and with laminin, to positively modulate neuronal differentiation. In one embodiment, heparan sulfate is added to the collagen mixture.

Composite collagen substrates with laminin and/or heparan sulfate all maintained a low level of GFAP positive glial cells, with initiation of astrocytic networking becoming more obvious at the later time point. In general, substrates that supported neuronal differentiation demonstrated a bare minimum of glial cells required to possibly support neuronal cell phenotype or survival.

Substrates that supported neuronal differentiation may result in enriched populations of neuronal cells comprising greater than 25%, 30%, 35%, 40%, 45%, 50%, 55%, 60%, 65%, 70%, 75%, 80%, 85%, 90%, 100%, or any intermediate percentage.

Enteric neurospheres demonstrated a tendency to differentiate into glia on PLL coated substrates as well as on composite collagen substrates in the absence of laminin and heparan sulfate. In contract, culture substrates with laminin and heparan sulfate promoted extensive neuronal differentiation while simultaneously supporting only a minimal glial cell population. Laminin and collagen IV coated coverslips positively modulated neuronal differentiation by increased number of neurites per neuron and longer neurite lengths compared to fibrillar collagen I (FIG. 2B-D, F-H).

Taken together, these results identify suitable 3D matrix compositions to deliver neuronal progenitor cells. Three dimensional hydrogel environments also provide the mechanical cues for neural differentiation, more readily translatable to in vivo conditions than infinitely stiff glass substrates.

The extracellular matrix (ECM) plays an enormous role in dictating stem cell fate. The ECM composition, structure and mechanical properties can all modulate progenitor cell differentiation. The adult mammalian myenteric ganglia are surrounded by an extracellular matrix primarily composed of collagen IV, laminin and a heparan sulfate proteoglycan, with enteric glia always in direct contact with the ECM. Enteric neurons also come in direct contact with this ECM, though much less frequently than glia. Laminin, fibronectin and proteoglycans are expressed within the embyonic gut to aid its colonization by vagal neural crest cells. Collagen IV is distributed in the developing nervous system along the neural crest. Additionally, laminin promotes neural cell adhesion and axonal outgrowth. Heparan sulfate is important for GDNF signaling in the gut, and stabilizes and influences neuronal differentiation in vitro.

It has been discovered that components of neural ECM can affect the differentiation of gut-derived neuronal progenitor cells of neural-crest lineage. Two timepoints were defined to identify early and late differentiation events—day 5 (early) and day 15 (late) based on previous experiments. Immunohistochemistry for βIII tubulin (neuron specific microtubule) and GFAP (Glial fibrillary acidic protein) was used to identify differentiated neurons and glia on coated culture substrata.

Substrates that supported glial differentiation may result in enriched populations of glial cells comprising greater than 25%, 30%, 35%, 40%, 45%, 50%, 55%, 60%, 65%, 70%, 75%, 80%, 85%, 90%, 100%, or any intermediate percentage.

Neuronal Subtype Differentiation

Neural stem cell transplantation is a promising therapeutic approach to repopulate neurons within enteric ganglia. A complete loss of neurons is reported in HSCR, and a partial loss of selective neuronal subtypes is documented in achalasia and stenosis. Several groups have injected enteric neuronal progenitor cells into experimental models of aganglionosis, demonstrating the feasibility of transplantation. However, there is inadequate focus on differentiation of progenitor cells into mature neuronal subtypes, and subsequent assessment of functionality. Here, we describe one embodiment of the invention, whereby we describe a novel method to bias differentiation of enteric neuronal progenitor cells in vitro, prior to transplantation.

The ECM microenvironment, consisting of collagens, laminin and proteoglycans, not only acts as a structural framework for cells, but also plays an active role in aiding neurotrophic signaling. In an embodiment of this invention, four ECM components (collagen I, collagen IV, laminin and heparan sulfate) were evaluated, three of which are known to be present in adult myenteric ganglia. Collagen IV has been documented to be favorable for neurite outgrowth and neuronal differentiation. Laminin has long been known for its neurite promoting activity, in central, peripheral, and enteric neurons. The role of the heparan sulfate proteoglycan in neuronal differentiation is also well documented, both developmentally and in regenerative medicine applications. Fibrillar Collagen I was used additionally in these studies for ease of gelation and incorporation of other ECM components within a 3D hydrogel.

Apart from composition, substrate elasticity has been demonstrated to affect the differentiation of adult neural stem cells, with neuronal differentiation reported between 100-500 Pa. ECM hydrogel compositions were adjusted in order to maintain their viscoelastic modulus within the range suitable for neuronal differentiation (FIG. 10, table). Structural architecture was verified using scanning electron microscopy, wherein the addition of collagen IV demonstrated the presence of network structures, similar to self-assembled collagen IV in the mammalian basement membrane. The addition of laminin did not alter the ultrastructure, because it was expected to coat collagen fibers evenly. Additionally, laminin was also not expected to alter the stiffness/viscoelasticity of the gels, given the manner of its interaction with the collagen. The glycosaminoglycan chains of heparan sulfate are documented to cross link between laminin and collagen IV, thereby pulling fibers into a more compact structure, and slightly increasing the viscoelasticity of ECM gels.

Smooth muscle cells within tissue engineered sheets drive the differentiation of enteric neuronal progenitor cells. Tissue engineered sheets provided a good modality to assess variability of differentiated neurons due to ECM composition as well as the functionality of differentiated neurons. The proximity to smooth muscle promoted the differentiation of enteric neuronal progenitor cells extensively. In vitro differentiation of neural stem cells in the presence of gut-derived factors has been demonstrated previously by us and others. Neurotrophic factors (NT-3, Neurturin, GDNF) and morphogens (BMP-2/4) capable of driving enteric neuronal progenitor cell proliferation and differentiation have been demonstrated to arise from the smooth muscle and mesenchyme of the developing and adult gut. Recently, the postnatal bowel was demonstrated to support the differentiation of enteric neuronal progenitor cells, strengthening the fact that cues for differentiation can be derived from the postnatal gut. Hence, it was expected that smooth muscle cells within the tissue engineered sheets would drive the differentiation of enteric neuronal progenitor cells. We evaluated all tissue engineered sheets to ensure that the constituent smooth muscle cells demonstrated a contractile phenotype expressing Smoothelin (FIG. 14B). Smoothelin expression has been previously demonstrated to be essential for contractility of smooth muscle. In line with the equivalent expression of smoothelin, myogenic electromechanical coupling integrity was also equivalent in the tissue engineered sheets (FIG. 14A-D) Similar patterns of contractions were observed in tissue engineered sheets in response to KCl, regardless of ECM composition.

The ECM modulates differential neuronal subtypes while supporting overall smooth muscle-driven neuronal differentiation. In the presence of the smooth muscle, enteric neuronal progenitor cells differentiated, and expressed similar amounts of pan-neuronal marker βIII Tubulin (FIG. 14A), suggesting that smooth muscle derived factors and substrate viscoelasticity were suitable for overall neuronal differentiation. However, on closer examination of neural subtypes, there was a differential expression of excitatory and inhibitory markers within tissue engineered sheets with varying ECM compositions (FIG. 14). Sheets containing laminin had a balanced expression of both ChAT and nNOS. Kinetics of Ach-induced contraction in laminin sheets was most similar to native tissue, indicating the presence of an increased viable cholinergic neuronal component in composite collagen/laminin sheets. Furthermore, attenuation of EFS-induced relaxation by L-NAME (~62%) was also kinetically similar to native tissue (~78%), indicating the presence of a nitrergic neuronal component.

Collagen I, in the absence of any other matrix components, was the ECM of choice when an enriched cholinergic neuronal population was required, with a significantly diminished nitrergic neuronal population (FIG. 14C-D). While these sheets demonstrated a robust TTX-sensitive Ach-induced contraction commensurate with the heightened ChAT protein expression, relaxation in response to an electrical field was diminished. Furthermore, there was minimal attenuation of relaxation upon the inhibition of nNOS, correlating with the low nNOS expression.

Substrates that supported cholinergic neuron differentiation may result in enriched populations of cholinergic neurons comprising greater than 25%, 30%, 35%, 40%, 45%, 50%, 55%, 60%, 65%, 70%, 75%, 80%, 85%, 90%, 100%, or any intermediate percentage.

Composite Collagen I/IV sheets had an enhanced nNOS protein expression, with an associated increase in EFS induced relaxation (FIG. 18B). AUC of relaxation in composite Collagen I/IV sheets was comparable to native intestinal tissue. However, both ChAT expression and contraction was lower in composite collagen sheets.

Substrates that supported nitrergic neuron differentiation may result in enriched populations of nitrergic neurons comprising greater than 25%, 30%, 35%, 40%, 45%, 50%, 55%, 60%, 65%, 70%, 75%, 80%, 85%, 90%, 100%, or any intermediate percentage.

The ECM is a framework upon which smooth muscle derived factors regulate differentiation of neural subtypes. We demonstrate a critical role of collagen I and collagen IV containing ECM environments in promoting excitatory and inhibitory motor neurons, respectively. The ECM microenvironment plays a role in modulating neurotrophic as well as morphogenetic signaling. Morphogenetic signaling via the BMP family expressed in fetal gut is important for the phenotypic diversity of enteric ganglia, including nitrergic and VIP-ergic neuron differentiation. Collagen IV is documented to modulate BMP signaling, and heparan sulfate modulates GDNF signaling in the gut. Immunoreactivity of neurotrophic factor, NT-3, has been observed in ganglia and in the ECM molecules surrounding them, suggesting a role for a Collagen IV-based ECM to modulate NT-3 signaling. The constituent smooth muscle phenotype in tissue engineered sheets was contractile, expressing smoothelin, and generating contractions and relaxations approaching ~60% of those generated by native intestinal tissue. Differentiation cues arising from the constituent smooth muscle cells drove enteric neuronal differentiation. Furthermore, it is likely that the ECM could act as a framework for smooth muscle-derived factors, enhancing or inhibiting their effects, resulting in the generation of differential neuronal phenotypes.

EXAMPLES

Reagents

All tissue culture reagents were purchased from Invitrogen (Carlsbad, Calif.) unless specified otherwise. Primary and fluorophore conjugated secondary antibodies were purchased from Abcam (Cambridge, Mass.). Rat tail type I collagen and natural mouse type IV collagen were purchased from BD Biosciences (Bedford, Mass.) and laminin was from Invitrogen (Carlsbad, Calif.). Heparan sulfate was purchased from Celsus Labs (Cincinnati, Ohio).

Isolation of Rabbit Enteric Neuronal Progenitor Cells and Intestinal Smooth Muscle Cells.

New Zealand white rabbits were euthanized using ketamine/xylazine. Smooth muscle cells were isolated and cultured using standard protocols (See, for example, Somara et al. Am J Physiol Gastrointest Liver Physiol. 2006; 291 (4):G630-9). For the isolation of enteric neuronal progenitor cells, 5 cm$^2$ biopsies were dissected from the jejunum, and retrieved in Hank's Buffered Salt Solution (HBSS) with 2× antibiotics/antimycotics and 1× gentamicin sulfate. Luminal content was cleaned and tissues were washed extensively with HBSS. Enteric neuronal progenitor cells were isolated from these tissues using a collagenase/dispase digestion method. (see, for example, Almond et al., Characterisation and transplantation of enteric nervous system progenitor cells. Gut. 2007; 56(4):489-96. PMCID: 1856871). Cells were plated on to bacterial petri dishes in neuronal growth media (Neurobasal+1× N2 supplement+1× antibiotics) following filtration through a 40 µm mesh.

Isolation and Culture of Rabbit Longitudinal Smooth Muscle Cells (LSMCs)

Rabbit sigmoid colon was removed by dissection, and relieved of fecal content. The tissue was kept on ice and moist with Hank's balanced salt solution (HBSS) containing antibiotics and sodium bicarbonate. The cleaned colon was slipped onto a plastic pipette. Blood vessels and adherent fat were picked off with forceps. Kimwipe® (Kimberly-Clark, Neenah, Wis.) wetted with HBSS was used to wipe the outer layer of the colon. Fine-tip forceps were used to pick off the longitudinal muscle layer from the colon and store them in ice-cold HBSS. The tissue was finely minced, digested twice with type II collagenase (0.1%) at 32° C. for 1 h, and filtered through a 500-µm Nytex® (Tetko, Elmsford, N.Y.) mesh. The filtrate was washed three times and plated in DMEM with 10% FBS, 1.5% antibiotics, and 0.5% L-glutamine onto regular tissue culture flasks.

Immunohistochemical Characterization of Rabbit Enteric Neurospheres

In order to characterize the initial phenotype of rabbit enteric neurospheres in culture, neurospheres were harvested by centrifugation at 1000 g for 10 minutes in microfuge tubes. The growth media was gently aspirated, and neurospheres were fixed with 3.7% neutral buffered formaldehyde and blocked with 10% horse serum. Primary antibodies for p75 (Millipore, Billerica Mass.), Sox2 and Nestin were incubated for 30 minutes at room temperature. Unbound antibody was washed using phosphate buffered saline (PBS), and appropriate fluorophore-conjugated secondary antibodies were incubated for an additional 30 minutes. Neurospheres were mounted using Prolong Gold antifade mounting medium (Invitrogen, Carlsbad Calif.), and visualized using an inverted Nikon TiE fluorescent microscope.

Rheological Characterization of ECM Hydrogels

Oscillatory rheometry (ATS RheoSystems) was used to measure viscoelastic moduli of ECM gels. 20 mm parallel base plates were used to perform a stress sweep of the sample at 1 Hz. ECM gels were allowed to gel in situ between the parallel plates at 37° C. The viscoelastic modulus was obtained from a linear region of the stress-strain curve, at strains lower than 10%, within the sensitivity ranges for torque and strain of the rheometer. 3-5 individually manufactured ECM gels were measured to determine an average viscoelastic modulus. Compositions that resulted in a matrix viscoelasticity within the range of 150-300 Pa were utilized for further experimentation, so as not to let stiffness be a variable in influencing neuroglial differentiation.

Characterization of Ultrastructure of ECM Hydrogels

Sample preparation of ECM hydrogels for scanning electron microscopy was adapted from Stuart et al. [31]. Gels were dehydrated through graded ethanol (10% to 100%). Hydrogels were dried at critical point using carbon dioxide exchange. The resulting dehydrated ECM discs were mounted onto metallic stubs with conducting carbon tape, sputter coated with gold, and visualized using an AMRAY 1910 Field Emission Scanning Electron Microscope. Constant working distance and magnification were maintained to image all samples. NIH Image J was used to measure and compare fiber diameters. Porosity was determined using Image J from micrographs obtained from at least three-independent samples of dehydrated ECM gels.

Tissue Engineering Innervated Intestinal Smooth Muscle Sheets

Briefly, 500,000 longitudinal smooth muscle cells were aligned uniaxially for 4 days on 35 mm diameter circular Sylgard molds containing wavy microtopographies. Enteric neurospheres were treated with Accutase to obtain single cell suspensions. 200,000 cells were resuspended in the appropriate ECM solution and overlaid on the aligned smooth muscle monolayer. Upon gelation, neuronal differentiation medium (neurobasal-A) was added, supplemented with B27 and 1% fetal bovine serum. Differentiation medium was exchanged every second day. Enteric neuronal progenitor cells were allowed to differentiate within the hydrogel for a period of 10 days. Smooth muscle cells compacted the ECM hydrogel over the next 10 days, forming ~1 cm long innervated smooth muscle sheets, anchored between silk sutures. Phase microscopy was used to image neuronal differentiation at the edge of the tissue engineered sheets.

Biochemical Characterization of Neuroglial Composition in Tissue Engineered Sheets At day 10, tissue engineered sheets were harvested in radioimmunoprecipitation buffer to isolate protein. Protein concentration was estimated spectrophotometrically using the Bradford assay. 20 μg of protein from each sample was resolved electrophoretically and transferred to polyvinylidene difluoride membranes. Membranes were blotted with antibodies for neuronal βIII Tubulin, neuronal nitric oxide synthase (nNOS), choline acetyltransferase (ChAT), and Smoothelin. β-Actin was used to confirm equal loading. HRP-conjugated secondary antibodies were used to visualize proteins using enhanced chemiluminescence.

Immunohistochemical Characterization of Neuron Composition in Tissue Engineered Sheets Tissue engineered sheets were fixed in 4% formaldehyde and washed extensively in glycine buffer. Immunohistochemical staining was performed following previously established protocols utilized for staining differentiated neurons within bioengineered tissues. Sheets were blocked with 10% horse serum and permeabilized in 0.15% Triton-X for 45 minutes. Permeabilized sheets were incubated with primary antibodies directed against Vasoactive Intestinal Peptide (VIP), ChAT and nNOS for 60 minutes at room temperature. Following antibody incubation, sheets were washed three times with phosphate buffered saline, pH 7.4. Tissue engineered sheets were incubated with appropriate fluorophore conjugated secondary antibodies for 45 minutes, washed in phosphate buffered saline and imaged using an inverted fluorescence microscopy (Nikon Ti-E, Japan). For a negative control, incubation with the primary antibody was skipped, and only fluorophore conjugated secondary antibodies were used to visualize background fluorescence.

Measurement of Physiological Function in Inntervated Tissue Engineered Sheets

Myogenic and neuronal functionality were assessed using real-time force generation as previously described [30, 33]. 4-5 individual tissue engineered sheets for each ECM composition were tested. Tissue engineered sheets were anchored between a stationary pin and measuring pin of a force transducer (Harvard Apparatus, Holliston Mass.) at 0% stretch. The organ bath maintained temperature at 37° C. An additional 10% stretch was applied using a vernier control. Tissues were immersed in 4 ml of medium, which was exchanged at the end of every experiment following a brief wash with fresh medium. Peak contraction or maximal relaxation was quantified following pharmacological or electrical stimuli, and compared between tissue engineered sheets with varying ECM compositions. Before each treatment, tissues were washed in fresh warm medium and allowed to equilibrate to a baseline. The following stimuli were used independently to assess physiological functionality of the tissue engineered sheets: 1) 60 mM Potassium chloride to assess electromechanical coupling integrity of the smooth muscle; 2) 1 μM Acetylcholine (contractile agonist); 3) Electrical field stimulation (5 Hz, 0.5 ms, 40V) applied using parallel plate platinum electrodes. Preincubation with neuronal blocker, tetrodotoxin (TTX) was used to dissect myogenic and neuronal components of contraction/relaxation. Preincubation with specific inhibitors were used to identify functional neuronal subtypes: 1) nNOS-blocker Nω-Nitro-L-arginine methyl ester hydrochloride (L-NAME; 300 μM); and 2) VIP-receptor antagonist [D-p-Cl-Phe6, Leu17]-Vasoactive Intestinal Peptide (VIP-Ra; 2 μM). Following stimulation and subsequent contraction/relaxation and recovery, tissues were washed with fresh medium, and allowed to re-establish a baseline before the next treatment. Equilibrated baseline was arbitrarily set to zero, to measure contraction/relaxation due to a stimulus.

Neurosphere Differentiation as a Function of Extracellular Matrix Composition

22×11 mm substrates were washed in Neutrad (Decon Labs, King of Prussia Pa.) and rinsed extensively in deionized water. Coverslips were sterilized by 70% ethanol, and subsequent UV exposure for 45 minutes. Coverslips were coated with poly-L-lysine (PLL; 1 mg/ml), PLL+10 µg/cm² type I collagen, PLL+10 µg/cm² type IV collagen or PLL+10 µg/cm² laminin. Composite coatings included:
- 5 µg/cm² Collagen I+5 µg/cm² type IV Collagen;
- 5 µg/cm² Collagen I+5 or 10 µg/cm² Laminin;
- 5 µg/cm² Collagen IV+5 or 10 µg/cm² Laminin;
- 5 µg/cm² Collagen I+5 µg/cm² Collagen IV+0.1 µg/cm² Heparan Sulfate (HS);
- 5 µg/cm² Collagen I+5 µg/cm² Collagen IV+5 µg/cm² Laminin+0.1 µg/cm² HS.

Uncoated glass substrates were seeded with rabbit colonic smooth muscle cells, and allowed to reach confluence. Rabbit enteric neurospheres were harvested and treated with Accutase to obtain a mixture of single cells as well as small neurospheres. 10,000 neuronal progenitor cells were harvested and plated on to coated coverslips. To stimulate differentiation induced via soluble smooth muscle factors, each plate was shared by one confluent smooth muscle coverslip along with a coated coverslip containing adhered neurospheres. Enteric neurospheres were allowed to differentiate for a period of fifteen days, with a supplementation of neuronal differentiation medium every 2 days (Neurobasal-A medium+1× B27 supplement+2% fetal calf serum+1× antibiotics).

Immunohistochemical Analysis of Neuronal and Glial Differentiation

Two time points were analyzed for neuronal and glial differentiation—day 5 and day 15 post initiation of differentiation. Medium was aspirated and cells on coverslips were fixed with 3.7 neutral buffered formaldehyde. Cells were permeabilized with 0.15% Triton-X 100 and blocked with 10% horse serum. βIII tubulin was used to stain neuronal cells, and glial fibrillary acidic protein (GFAP) was used to stain glial cells. Primary antibodies were incubated for 1 hour at room temperature and unbound antibody was washed with PBS. Fluorophore conjugated secondary antibodies (FITC-anti mouse and TRITC-anti rabbit) were used to visualize fluorescence using an inverted Nikon TiE fluorescent microscope. Staining with FITC-conjugated secondary antibody without the primary antibody was used as a negative control. Confluent smooth muscle coverslips were stained with neuronal or glial markers to avoid a false positive staining while identifying differentiated neurons or glia.

Data Analysis

Neurite lengths were measured from individual 10× micrographs obtained at the same amplifier gain and exposure. Neurites were identified primarily by expression of immunoreactivity for βIII tubulin concurrently with neuronal morphology. Up to five sequential fields of view were measured on each coverslip starting from one edge to the other, covering the area of the coverslip. All cells were measured on each coverslip, covering the entire area of the neuronal coverslip. The number of neurites measured for each substrate coating varied between 20-50 readings. The length of the longest neurite from each cell was measured using NIH Image J using the freeform tool. Neurite lengths between coatings were compared using one way ANOVA, with Bonferroni post-test to identify a significant difference ($p<0.05$) in neurite lengths by varying culture substrata. GFAP immunofluorescence was quantified using the Nikon Elements imaging software. Mean red (TRITC) fluorescence was calculated from 10× micrographs, using a constant rectangular area tool that covered 100% of the field of view. Multiple (at least 5) sequential fields of view at the same magnification were chosen for each sample to obtain mean fluorescence. One way ANOVA with Bonferroni post-test was used to identify a significant difference in red fluorescent intensity between coated culture substrata. GraphPad Prism 5.1 for Windows (San Diego, Calif.) was used to perform statistical analysis. All statistics are from experiments between 3-5 individual sets, with multiple micrographs within each set. Reported numbers are mean±standard error of the mean. For neuronal subtype analysis, densitometry on western blots was performed using BioRad Quantity One (Hercules, Calif.). Raw data was acquired from the force transducer at 1000 samples/second. Second order Savitsky-Golay smoothing was applied to data using GraphPad Prism 5.0 for Windows (GraphPad Software, San Diego, Calif.). Area under the curve (AUC) was measured from the time of addition of pharmacological agonist/electrical field to the end of the contraction/relaxation response. Extent of inhibition by pharmacological inhibitors was calculated by expressing the AUC of contraction/relaxation in the presence of the inhibitor as a percentage of the AUC in the absence of the inhibitor. One way ANOVAs with Tukey post-tests were used to compare means using GraphPad Prism. $p \leq 0.05$ was considered significant. Physiological evaluation and densitometry was carried out between 3-5 tissue engineered sheets within each experimental set; all values are expressed as mean±SEM.

Neuroglial Differentiation

Initial Phenotype of Rabbit Enteric Neurospheres

Upon digestion of rabbit jejunal biopsies with dispase, near single cell suspensions were obtained by filtration through 70 µm and 40 µm meshes. Single cells were approximately 7 µm in diameter. These cells were plated in non-adherent culture dishes. Over the course of two weeks post plating, rabbit enteric neuronal progenitor cells aggregated and proliferated in culture and formed floating spherical structures, called enteric neurospheres (FIG. 1A). Average neurospheres were 98.17±8.33 µm (n=34) two weeks post plating. The neurospheres continued to grow and aggregate, approaching 200-300 µm, whereupon they were broken down by trituration. Upon immunohistochemical examination, the cells within enteric neurospheres were positive for the low affinity nerve growth factor receptor $p75^{NTR}$ (FIG. 1B). They were additionally also positive for Sox2 (FIG. 1C, SRY related homeobox factor 2) and Nestin (FIG. 1D), a neuroepithelial stem cell marker. The results indicate that neurospheres derived from the rabbit intestine following this procedure contained neural-crest derived cells, capable of differentiation in to enteric neurons and/or enteric glia.

Figure 1:
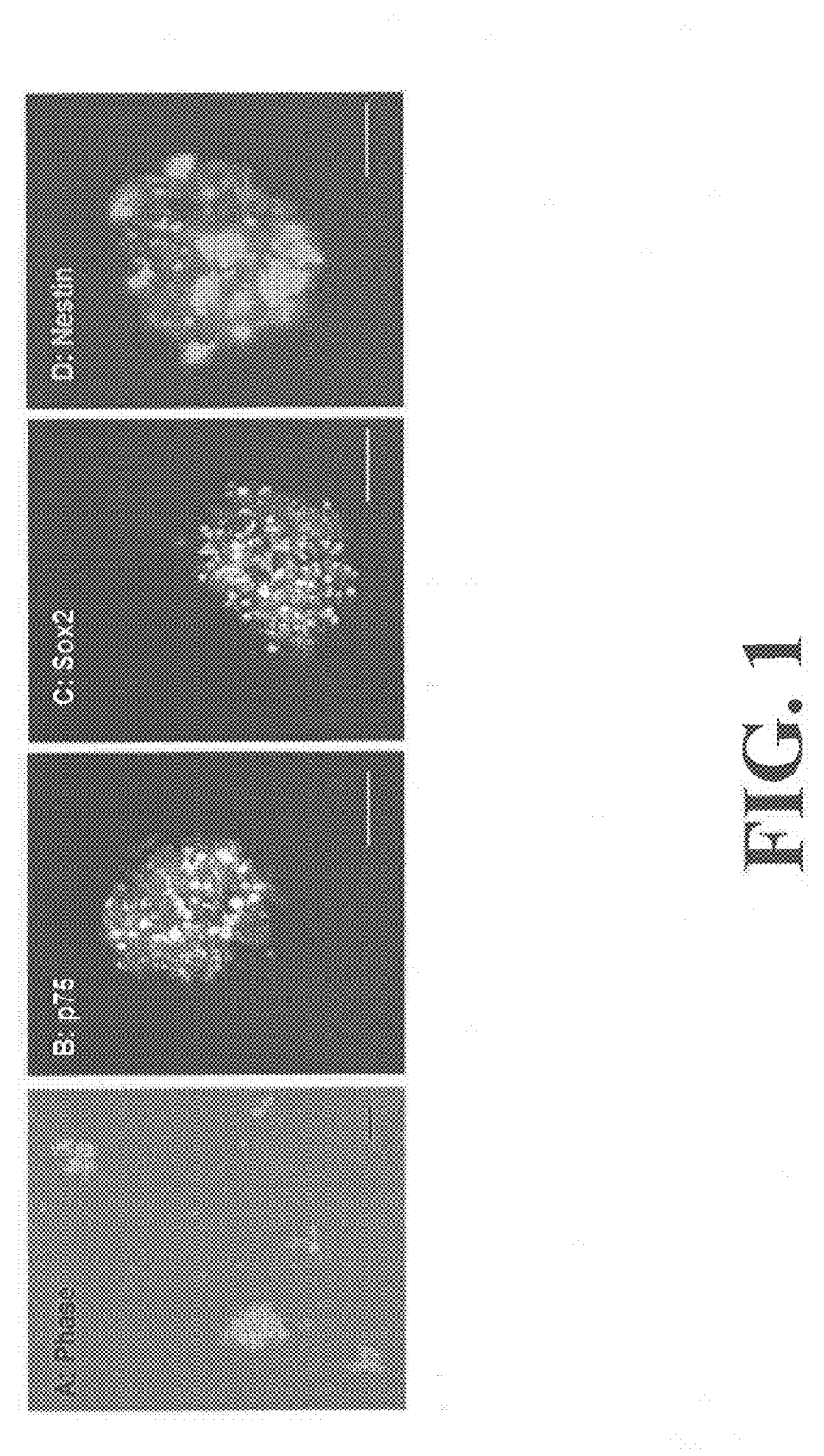
FIG. 1 A-D are micrographs of rabbitenteric neuro spheres

Neuronal progenitor cells were isolated from full thickness biopsies of adult rabbit jejunums that aggregate in culture to form floating spherical colonies, dubbed enteric neurospheres (FIG. 1A). The enteric neurospheres were comprised of cells positive for p75, Sox2 and Nestin (FIG. 1 B-D). The presence of $p75^{NTR}$ confirms the neural-crest lineage of the isolated cells. The presence of Sox2 and Nestin confirms the progenitor status of the isolated cells, indicating that these cells are similar to enteric neuronal progenitor cells previously isolated from the gut that have the potential to differentiate into both neurons and glia.

Neuronal Differentiation on Individual ECM Substrates (Collagen I, Collagen IV or Laminin)

Poly-L-lysine (PLL) coating was a pre-requisite to enteric neurosphere adhesion to glass substrates. Glass coverslips that lacked any coating did not support enteric neurosphere adhesion sufficiently to differentiate into neurons or glia. In order to maintain uniformity, all coverslips were initially coated with PLL and additionally with laminin, collagen I or collagen IV. All coated coverslips required between 2-4 hours for enteric neurospheres to attach.

Figure 2:
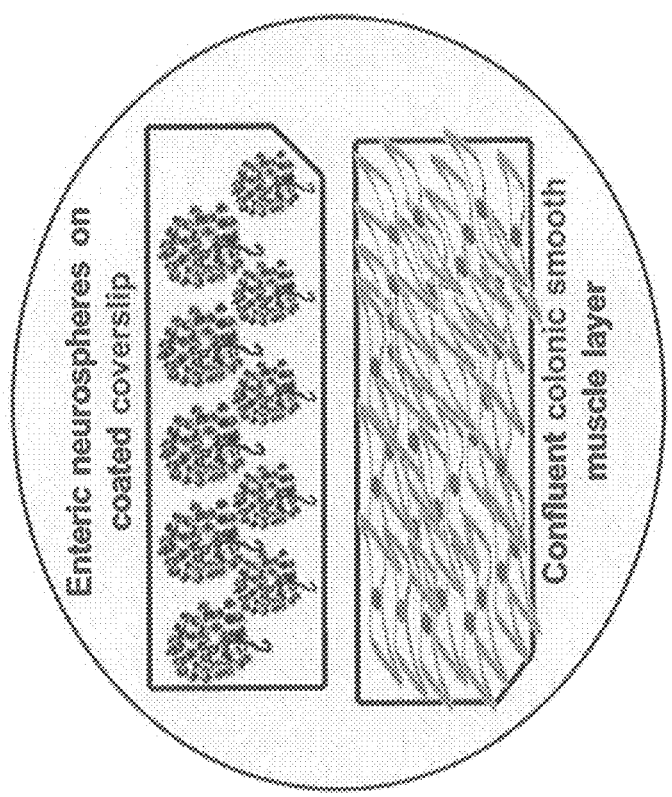
FIG. 2 is a schematic illustration of enteric neuro sphere differentiation as a function of extracellular matrix (ECM) composition: 22×11 mm coverslips were coated with poly-L-lysine (PLL), collagen I, collagen IV, laminin or heparan sulfate individually or in combination. Enteric neurospheres were allowed to adhere to the coated coverslips for 6 hours. Separately, uncoated glass coverslips were seeded with colonic smooth muscle cells, and allowed to grow to confluence. In order to stimulate differentiation of enteric neurospheres, a coverslip containing confluent smooth muscle was placed within the same dish, so the two coverslips shared soluble factors.

Enteric neurospheres on coated coverslips were allowed to differentiate initially using neuronal differentiation medium alone. However, several sets of experiments demonstrated no morphological evidence of differentiation at the day 15 timepoint. Thereby, in order to render the soluble environment conducive to differentiation, a confluent coverslip containing colonic smooth muscle cells was placed in the same culture dish (FIG. 2). The neuronal coverslip (coated with ECM substrate and containing enteric neurospheres) and the smooth muscle coverslips thereby shared soluble factors. The addition of the smooth muscle coverslip marked the initiation of differentiation (day 0).

Morphological evidence of neuronal or glial differentiation was readily visible by day 5. A later time point (day 15) was identified to study the development of mature neurons or glia in vitro as a function of ECM composition. During the differentiation process, the culture dishes remained undisturbed till the early time point (day 5) or the late time point (day 15), except for medium supplementation. Neuronal differentiation was identified by immunofluorescent staining of the neuronal coverslip at either day 5 or day 15 with an antibody directed against βIII Tubulin.

Figure 3:
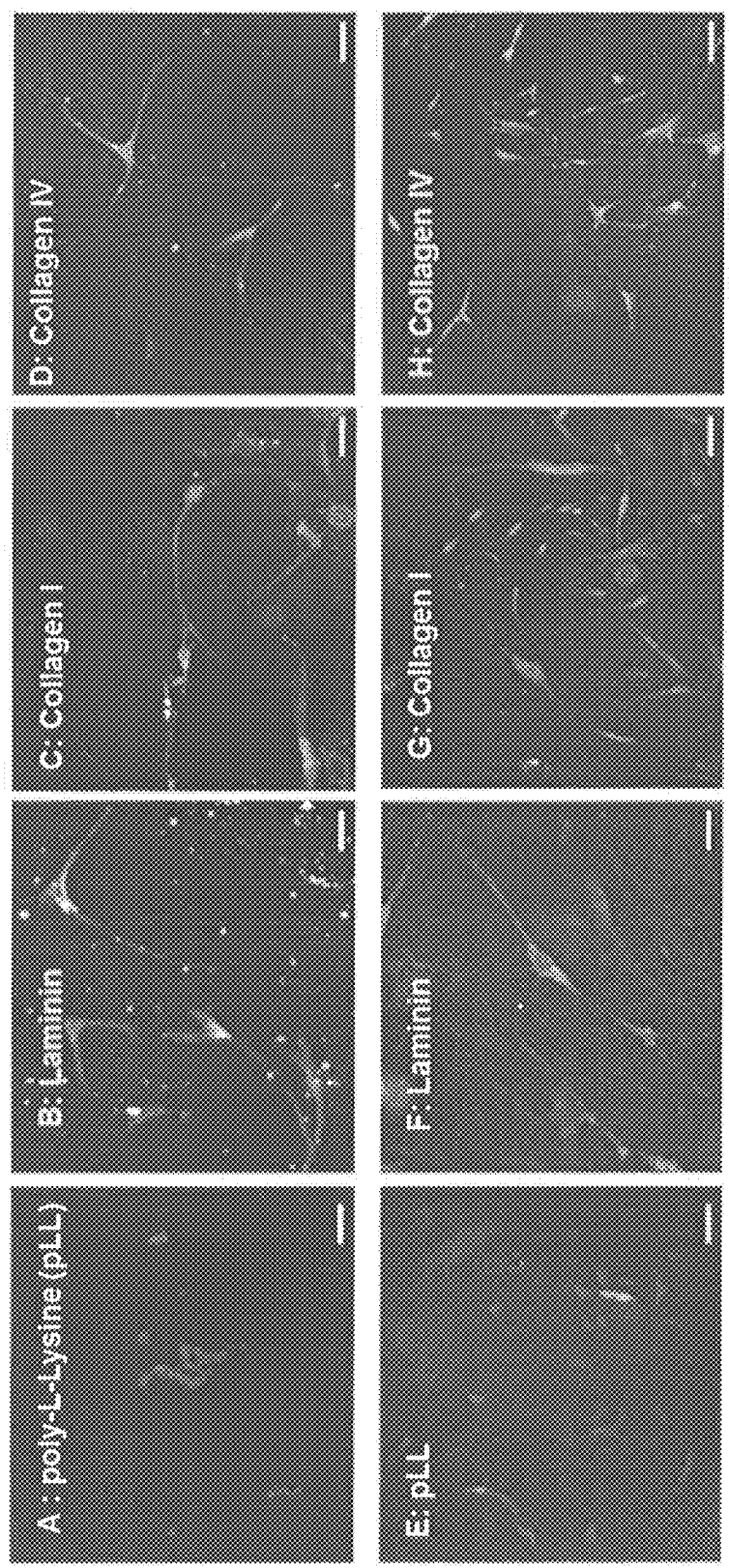
FIG. 3 illustrates neuronal differentiation on individual coated coverslips—βIII Tubulin antibody (white) was used to visualize neurons on day 5 (Figs. A-D) and day 15 (Figs.

Day 5 Timepoint: Even in the presence of smooth muscle, enteric neurospheres on PLL remained undifferentiated, with some progenitor cells within neurospheres expressing low levels of βIII tubulin (FIG. 3A). However, with the addition of laminin, collagen I or collagen IV to PLL on the culture substrata, neuronal differentiation was evident by day 5 (FIG. 3B-D). Neurite lengths varied non-significantly between 193 µm and 288 µm on ECM substrata at the early time point (FIG. 9A). Neurons on collagen IV and laminin coated coverslips demonstrated a higher level of branching (two or more neurites per cell; FIG. 3B,D).

Neurospheres and neuronal progenitor cells attached to the PLL coated coverslips, and stayed attached at day 5, but did not initiate neuronal differentiation. However, glial differentiation was readily visible by day 5, and improved by day 15 (FIG. 3A,E; FIG. 6A,E). Enteric neurospheres on PLL substrates indicated a preference towards glial differentiation versus neuronal differentiation.

Day 15 Timepoint: At the day 15 timepoint, neurospheres on PLL coverslips barely initiated neuronal differentiation, evidenced by a flatter morphology and the appearances of faint tubulin-positive extensions (FIG. 3E). With the addition of laminin, collagen I or collagen IV, neurite lengths were significantly longer compared to PLL ($p<0.001$). Differentiated neurons on laminin coverslips demonstrated the longest neurite extensions ($326.9\pm13.25$ µm, n=27, FIG. 3F), significantly longer than collagen I or collagen IV ($p<0.05$, FIG. 9A). By day 15, neurons on collagen I-coated coverslips still had no significant branching compared to those on collagen IV-coated coverslips (FIGS. 3G-H).

Neuronal Differentiation on Collagen Laminin Substrates

In the next set of experiments, combinations of collagens and laminin were evaluated. Two concentrations of laminin were evaluated to identify the minimum amount of laminin required to influence neuronal differentiation. Coverslips were coated with either collagen I or collagen IV with 5 µg/cm$^2$ or 10 µg/cm$^2$ of laminin. The addition of laminin enhanced neuronal differentiation when compared to individual collagen substrates (compare FIG. 4 with FIG. 3), but no significant difference was observed in neurite length between the two concentrations of laminin.

Collagen I and Laminin: At the day 5 timepoint, addition of laminin to collagen I increased the number of progenitor cells undergoing neuronal differentiation, but did not alter neuronal branching or neurite lengths significantly (FIG. 4A,B,E,F). At the day 15 timepoint, significantly ($p<0.05$) enhanced neuronal differentiation was observed compared to collagen I. Neurite lengths on collagen-laminin substrates at day 15 (280 µm-290 µm; n=27-34) were longer than collagen I substrates ($235.5\pm10.05$ µm; FIG. 9B).

Collagen IV and Laminin: The addition of laminin to collagen IV enhanced neuronal differentiation when compared to coverslips coated individually with collagen IV only (compare FIG. 4C,D,G,H to FIG. 3D,H). At the day 5 timepoint, the addition of laminin increased the number of cells undergoing neuronal differentiation. No significant difference was observed in neurite lengths at day 5 (247 µm-288 µm; FIG. 9B). At the day 15 time point, coverslips coated with both collagen IV and laminin had significantly ($p<0.05$) longer neurites (324 µm compared to 281 µm, FIG. 4G-H). Initiation of inter-neuronal networking was also observed. There was no observable or significant difference in neurite lengths between the two concentrations of laminin used (5 µg/cm$^2$ or 10 µg/cm$^2$; FIG. 9B).

Neuronal Differentiation on Composite ECM Substrates with Laiminin and Heparan Sulfate In this additional set, the effect of a combination of collagens on neuronal differentiation was investigated. Composite coatings were evaluated with a 2:1 mix of Collagen I/Collagen IV as the base. This composite collagen base was evaluated first. Additionally, neuronal differentiation was evaluated on substrates that included laminin and/or heparan sulfate in combination with composite collagen.

Heparan sulfate interacted with both collagen IV and with laminin to positively modulate neuronal differentiation, evidenced by the enhanced neurite lengths and initiation of neuronal networking (FIG. 4 A-H). Composite collagen substrates with laminin and/or heparan sulfate all maintained a low level of GFAP positive glial cells, with initiation of astrocytic networking becoming more obvious at the later time point.

Composite Collagen I/Collagen IV: Several cells underwent neuronal differentiation (FIG. 5A, E; similar to individual coatings of either collagen I or collagen IV), but neurite lengths were significantly shorter on composite collagen substrates at day 5. Neurite lengths measured at $156\pm7.23$ µm on day 5. At day 5, neuronal differentiation progressed and individual neurons had multiple branches and long neurites (FIG. 5E). Neurite lengths averaged at $241.2\pm9.387$ µm on day 15 (FIG. 9C).

Addition of Laminin: Addition of laminin to composite collagen substrates increased the number of differentiated neurons visible by day 5 (FIG. 5B). Neurite lengths were significantly ($p<0.05$) longer on substrates containing laminin ($215\pm7.57$ µm; n=43). At the day 15 time point, substrates containing composite collagen and laminin demonstrated significant clustering of neurons (FIG. 5F), with an additional 71 µm increase in neurite length, averaging at $286.8\pm9.521$ µm, n=50.

Addition of Heparan Sulfate: Addition of heparan sulfate also dramatically increased the number of progenitor cells undergoing neuronal differentiation by day 5 (FIG. 5C). Average neurite lengths on substrates containing heparan sulfate along with composite collagen was $212.8\pm9.46$ µm; n=43 at day 5. At day 15, the initiation of neuronal networking was visible with βIII Tubulin staining (FIG. 5G).

Addition of Laminin and Heparan Sulfate: The addition of laminin and heparan sulfate together with the composite collagen increased the number of differentiated neurons as well as the length of the individual neuronal processes and neurite branching (FIG. 5D). At day 15, initiation of neuronal networking with significant clustering of neurons was observed (FIG. 5H). Neurite lengths were significantly longer (325±19.37 μm) compared to composite collagen alone (FIG. 9C).

Glial Differentiation on Individual ECM Coatings (Collagen I, Collagen IV or Laminin)

In addition to neuronal differentiation studies described above, glial differentiation was also studied as a function of ECM composition of culture substrata. Enteric neurospheres were plated on to coated coverslips in duplicate, and one coverslip was used to evaluate neuronal differentiation while a duplicate coverslip was used to evaluate glial differentiation. A primary antibody directed against Glial fibrillary acidic protein (GFAP) was utilized to identify glial differentiation. Fluorescent microscopy was used to visualize differentiated glia, using a TRITC fluorophore conjugated secondary antibody. The Nikon documentation software was used to calculate mean red fluorescence indicating the number of differentiated glia in a field of view of constant area.

The presence of several axolemmal fragments can arrest the proliferation of glia. This is in line with the low levels of GFAP immunofluorescence observed on substrates that supported extensive neuronal differentiation. The only substrates that supported differentiation of enteric neuroglial progenitor cells into glia extensively were PLL and individual coatings of collagen I/IV. Neuronal differentiation was present on these substrates, but not as extensively as any of the other composite coatings that included laminin and heparan sulfate.

Day 5 Timepoint: In the presence of smooth muscle, enteric neurospheres on PLL coated coverslips demonstrated significant GFAP staining by day 5 (15.29±1.29 AU; FIG. 6A). In contrast, enteric neurospheres on PLL coverslips did not demonstrate significant neuronal differentiation at day 5, indicating the preferential differentiation in to glia at the early time point on PLL coverslips. With the addition of laminin, enteric neurospheres demonstrated highly significantly reduced GFAP staining (0.3825±0.2 AU). Undifferentiated neurospheres on the laminin coverslips contained several progenitor cells that were positive for GFAP (FIG. 6B). On the same laminin coated coverslips, neuronal differentiation was extensive at the early timepoint, indicating an early preference for neuronal differentiation in the presence of laminin (FIG. 3B). Minimal glial differentiation was observed on either of the collagen substrates (FIG. 6C-D).

Day 15 Timepoint: By the late day 15 time point, PLL coated coverslips had the highest number of glia, indicated by a highly significant ($p<0.0001$) GFAP fluorescent intensity, averaging at 28.56±1.14 AU (FIG. 6E, 9D). Glia were apparent on ECM-coated coverslips as well, but to a lower extent than on PLL. In contrast to day 5, laminin coated coverslips demonstrated the presence of several glia at the day 15 time point and a robust GFAP fluorescent intensity was observed (FIG. 5F, 16.54±0.32 AU). Several glia were observed by day 15 on each of the collagen substrates, with fluorescence ranging from 11.84 to 13.38 AU. (FIGS. 6G-H).

Glial Differentiation on Collagen-Laminin Substrates

Similar to neuronal differentiation, glial differentiation was evaluated on substrates that were coated with either collagen I or cCollagen IV with laminin. The addition of laminin to collagen coated coverslips did not inhibit glial differentiation. Several differentiated glia were observed on day 5 (8.4±0.75-14.08±0.3 AU) on collagen-laminin substrates (FIG. 7A-D). There was no significant difference in the number of GFAP positive cells at the early time point with the addition of laminin (5 μg/cm$^2$ or 10 μg/cm$^2$) to either collagen I or collagen IV substrates FIG. 9D). Robust GFAP expression (12.6±1.29-14.22±1.01 AU) was observed at the day 15 time point on all collagen-laminin substrates, not significantly different from one another (FIG. 7E-H).

Glial Differentiation on Composite ECM Substrates with Laminin and Heparan Sulfate Glial differentiation was evaluated by varying the culture substratum with a combination of collagen I and IV. Additionally, the effect of the addition of laminin and/or heparan sulfate was also studied on glial differentiation.

Composite Collagen I/Collagen IV: Glial differentiation peaked on day 5, on coverslips coated with the collagen I/IV mixture (FIG. 8A). Red fluorescence (15.75±0.49 AU) was comparable to that on PLL coated coverslips at day 5 (FIG. 9D). In contrast, neuronal differentiation on composite collagen coated coverslips was poor at the early time point, indicating a preferential differentiation into glia early on. By day 15, initiation of clustering of glial cells was observable (FIG. 8E), with no significant increase in red fluorescence.

Addition of Laminin and/or Heparan Sulfate: Early glial differentiation at day 5 was significantly reduced (10.16±0.8 to 11.06±0.5) with the addition of laminin and/or heparan sulfate to composite collagen substrates (FIG. 8B-D). In contrast, these substrates supported neuronal differentiation extensively (compare FIG. 8A-D to FIG. 5A-D), indicating a preferential neuronal differentiation at the early time point. At the later day 15 time point, a non-significant increase in the number of glia and thereby increase in red fluorescence was observed (FIG. 8E-H, FIG. 9D).

Neuronal Subtype Differentiation

Ultrastructure and Viscoelastic Properties of ECM Hydrogels: All compositions of ECM hydrogels gelled at 37° C. within 30 minutes. Scanning electron micrographs revealed a fibrous structure in type I Collagen gels (FIG. 10A). The fibers were randomly oriented, with diameters averaging at 478.3±19.31 μm. With the addition of type IV Collagen, network-like structures were observed (FIG. 10B). Cables of fibers within the networked structures were thicker, with average diameters of 714.8±36.67 μm. Addition of laminin to the hydrogels did not alter the ultrastructure or the networked suprastructure (FIG. 10C). With the addition of heparan sulfate, the fibers within the networked structures were pulled more tightly together and cabled (FIG. 10D). The dehydrated ECM gels displayed a porous appearance, with average porosity ranging from 40.77%-43.95% (FIG. 1, table).

Viscoelastic moduli were measured in hydrated ECM gels using oscillatory rheometry. Type I Collagen gels had increasing viscoelastic moduli with increasing collagen concentration ranging from 72.6±4.86 Pa (800 μm/ml) to 182.3±2.6 (1600 μm/ml) to 424±2 Pa (3200 μm/ml). The addition of 200 μm/ml collagen IV to 800 μm/ml collagen I increased the modulus of the gels to 236±13.53 Pa. The addition of laminin had no effect on viscoelastic moduli (compare 236±13.53 Pa to 220.7±16.27 Pa). 10 μm/ml of heparan sulfate caused an increase in the modulus of ECM hydrogels (287±20.11 Pa, $p<0.05$). FIG. 1 (table) summarizes that the final ECM gels evaluated had viscoelastic moduli ranging from 182 Pa to 287 Pa.

Neuronal Differentiation in Engineered Innervated Intestinal Smooth Muscle Sheets:

Uniaxially-aligned smooth muscle cells compacted overlaying ECM hydrogels over 10 days in culture as described before. The resultant tissue engineered sheets were ~1 cm long, and a few cell layers thick. In the presence of smooth muscle, the enteric neuronal progenitor cells differentiated within the ECM hydrogel. Neuronal differentiation was identified morphologically by microscopic examination at day 10, demonstrating similar differentiation profiles expressed by enteric neuronal progenitor cells, both in vitro and in tissue engineered constructs. Several differentiated neurons were observed in tissue engineered sheets, regardless of the ECM composition (FIG. 11). Arrows in the figures indicate numerous instances of neuronal clustering and preliminary neuronal networking.

Neuronal Composition in Engineered Innervated Intestinal Smooth Muscle Sheets:

Immunoblotting was used to assess neuronal composition within tissue engineered innervated intestinal smooth muscle sheets. Blotting for β-actin demonstrated that equal amounts of protein were assayed. Representative blots for each protein are shown, indicating the approximate molecular weight at which they appear on the gels (FIG. 12E). Contractile phenotype of constituent smooth muscle was demonstrated by the similar expression of smoothelin, within the tissue engineered sheets (FIG. 12B). The expression of Smoothelin was constant, regardless of the ECM composition of the sheets, indicating that the constituent smooth muscle cells maintained a contractile phenotype.

Neuronal Differentiation: Pan neuronal marker βIII Tubulin expression was similar amongst all tissue engineered sheets, despite the ECM composition (FIG. 12A). This suggested that irrespective of the ECM composition, neuronal differentiation of enteric neurospheres proceeded similarly in the presence of smooth muscle cells. βIII Tubulin expression ranged from 21.65±1.43 AU-28.98±0.85 AU. βIII Tubulin expression was similar amongst various ECM gel compositions (ns; FIG. 12A), indicating similar neuronal differentiation.

Cholinergic Neurons: Choline acetyltransferase (ChAT) expression was used to detect the presence of cholinergic neurons (FIG. 12C). Collagen I (33.73±1.13 AU) and collagen I/IV/laminin (28.82±1.21 AU) sheets had a significantly elevated expression of ChAT compared to sheets with composite collagen and/or heparan sulfate. Immunoblotting demonstrated an enriched cholinergic neuron population in tissue engineered sheets manufactured with collagen I only or composite collagen I/IV with laminin. The presence of cholinergic neurons was additionally confirmed using immunohistochemistry (FIG. 13E-H).

Nitrergic Inhibitory Motor Neurons: Neuronal nitric oxide synthase (nNOS) expression was used to detect the presence of inhibitory nitrergic motor neurons (FIG. 12D). Sheets with collagen IV (with or without laminin/heparan sulfate) had a significantly higher nNOS expression ranging from 26.37±1.29 AU-28.15±2.69 AU. Conversely to ChAT, collagen I sheets had minimal nNOS expression (11.33±2.85 AU). Presence of nNOS was additionally confirmed using immunohistochemistry (FIG. 13I-L).

VIP-Ergic Inhibitory Motor Neurons: Vasoactive intestinal peptide (VIP) motor neurons were identified using immunohistochemistry. VIP neurons were abundant, with increased immunofluorescence in composite hydrogels with laminin and heparan sulfate (FIG. 13A-D).

Substrates that supported peptidergic neuron differentiation may result in enriched populations of peptidergic neurons comprising greater than 25%, 30%, 35%, 40%, 45%, 50%, 55%, 60%, 65%, 70%, 75%, 80%, 85%, 90%, 100%, or any intermediate percentage.

Agonist Induced Contractility of Tissue Engineered Innervated Smooth Muscle Sheets Potassium Chloride-Induced Contraction: Electromechanical coupling integrity of constituent smooth muscle cells was first evaluated using potassium chloride (KCl). KCl treatment elicited rapid contractions that were sustained for ~5 minutes (FIG. 14). Peak maximal contraction in response to KCl was similar between the different tissue engineered sheets (FIG. 14A-D), ranging from 279.5±4.79 μN to 296.5±6.26 μN. This correlated with the equivalent expression of contractile smooth muscle marker, Smoothelin, indicating that the constituent smooth muscle cells within the tissue engineered sheets maintained a contractile phenotype regardless of ECM composition. Furthermore, KCl-induced contractions in tissue engineered sheets were similar to native rabbit intestinal tissues (FIG. 14E) in time course, but slightly reduced in magnitude. Peak KCl-induced contractions in native tissue averaged 373.5±10.63 μN. KCl-induced contraction was unaffected by pre-treatment with neuronal blocker TTX (grey traces; FIG. 14), indicating myogenic electromechanical coupling integrity. FIG. 16F demonstrates that the area under the curve of contraction was similar in all tissue engineered sheets, and was significantly higher in native rabbit intestinal tissues. Although reduced in magnitude compared to native tissue, KCl-induced contractions were similar among the different tissue engineered sheets, indicating a robust contractile smooth muscle phenotype unaffected by the ECM composition.

Acetylcholine-Induced Contraction: Exogenous addition of 1 μM Acetylcholine (Ach) was used to simulate agonist-induced contraction. All tissue engineered sheets contracted in response to Ach, and sustained contractions up to ~5 minutes post stimulation with Ach (FIG. 15A-D). Tissue engineered sheets with composite collagen I/IV with laminin had a significantly elevated peak maximal Ach-induced contraction (FIG. 15C; 232.9±8.167 μN), as well as an elevated area under the curve of contraction (47606±2054 AU). Magnitude of Ach-induced contraction was still significantly lower compared to contraction in native tissue (342.6±3.15 μN; 70448±5876 AU). However, the time course of contraction was very similar to native tissue in tissue engineered sheets containing laminin, reaching maximal contraction within a minute of agonist stimulation. Collagen I sheets also had an elevated Ach-induced contraction (FIG. 15A; 238.9±13.72 μN; 42668±2172 AU) corresponding to the elevated ChAT protein expression. However, the kinetics of contraction did not match native tissue.

In order to estimate the smooth muscle (myogenic) component of Ach-induced contraction, neurotoxin TTX was used as a pretreatment (grey traces, FIG. 15). Area under the curves of contraction was compared with and without TTX pre-treatment in order to estimate % inhibition (FIG. 15F). Percent inhibition of Ach-induced contraction in the presence of TTX was highest in two ECM conditions: i) collagen I sheets (72.77±2.45%); and ii) collagen I/IV/laminin sheets (60.58±1.66%). These values of % inhibition were similar to that observed in native tissue (72.73±3.66%) upon TTX-pretreatment. This increased neuronal contribution to Ach-induced contraction also correlated with the elevated protein expression of ChAT in collagen I and composite collagen I/IV/laminin sheets (FIG. 12E, G). TTX-pretreatment inhibited Ach-induced contraction to a significantly lower extent in collagen I/IV±heparan sulfate sheets, ranging from 48.36±4.36% (Heparan sulfate) to 50.31±4.22% (collagen IV; FIG. 15F).

Relaxation in Engineered Innervated Sheets in Response to Electrical Field Stimulation:

Electrical field stimulation (EFS) at 5 Hz, 0.5 ms was used to stimulate neurons within the tissue engineered sheets to produce relaxation of smooth muscle (FIG. 16). The extent of relaxation was quantified as area under the curve of relaxation. Extent of relaxation significantly varied amongst the tissue engineered sheets with varying ECM compositions. Sheets bioengineered with collagen IV, which displayed elevated nNOS expression, had higher relaxation compared to sheets bioengineered with collagen I only (compare 109693±8465 AU in collagen I/IV sheets to 23142±4921 in collagen I sheets). Sheets containing laminin and/or heparan sulfate also had significantly elevated relaxation compared to collagen I sheets (68395-69025 AU). In response to EFS, native tissues relaxed generating 101550±11279 AU. Tissue engineered sheets with collagen IV and/or laminin and/or heparan sulfate additionally had a time course of relaxation most similar to native tissue. Maximal relaxation was achieved within 2 minutes of EFS, and a subsequent recovery of basal force was complete within 10 minutes. Upon pre-treatment with TTX, EFS-induced relaxation was inhibited entirely (grey traces, FIG. 16).

Inhibition of Nitric Oxide Synthase: In order to identify the presence and functionality of nitrergic neurons, an inhibitor of nitric oxide synthase (L-NAME) was used (grey traces, FIG. 17). Percent inhibition was determined by comparing areas under the curves of maximal relaxation with and without the L-NAME pre-treatment. Percent inhibition with L-NAME treatment was the lowest in collagen I sheets (33.37±8.37%; grey trace, FIG. 17A). This corresponded to the low protein expression of nNOS in collagen I sheets compared to sheets containing collagen IV (FIG. 12D). In contrast, the inhibition of nNOS activity attenuated relaxation up to 61.71±2.82% (grey trace, FIG. 17B) in collagen I/IV sheets. In sheets containing laminin and heparan sulfate, % inhibition with L-NAME varied between 62.28±2.75% (laminin, FIG. 17C) to 57.16±1.91% (heparan sulfate). This inhibition is significantly elevated compared to collagen I sheets, corresponding to the increased expression of nNOS observed in the collagen I/collagen IV sheets (FIG. 12C). Native tissues had a higher % inhibition with L-NAME (78.02±2.85%).

Inhibition of the VIP-Receptor: The functionality of VIP-ergic neurons was assessed using a VIP receptor antagonist (VIP-Ra). Pre-treatment with VIP-Ra inhibited maximal relaxation in all tissue engineered sheets to varying extents ranging from 55.55±3.92%-65.92±5.38% (grey traces, FIG. 18). Inhibition of EFS-induced relaxation indicated the presence of differentiated VIP-ergic neurons in tissue engineered sheets.

The section headings used herein are for organizational purposes only and are not to be construed as limiting. While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

The invention claimed is:

1. A method of preparing an innervated smooth muscle construct, the method comprising:
    obtaining a population of longitudinal smooth muscle cells;
    culturing the longitudinal smooth muscle cells to form a uniaxially-aligned smooth muscle sheet;
    obtaining a population of neural stem cells
    and
    co-culturing the neural stem cells and the uniaxially-aligned smooth muscle sheet on a hydrogel substrate comprising at least one of collagen, laminin and heparan sulfate.

2. The method of claim 1 wherein the step of culturing the longitudinal smooth muscle cells further comprises culturing the muscle cells on a mold containing a wavy microtopography to form the uniaxially-aligned smooth muscle sheet.

3. The method of claim 1 wherein the hydrogel comprises collagen.

4. The method of claim 1 wherein the hydrogel comprises at least 800 µg/ml of collagen type I.

5. The method of claim 4, wherein the hydrogel comprises between about 800 µg/ml and about 1600 µg/ml collagen I.

6. The method of claim 1 wherein the hydrogel further comprises at least 200 µg/ml of collagen type IV.

7. The method of claim 1 wherein the hydrogel further comprises at least 5 µg/ml of laminin.

8. The method of claim 1 wherein the hydrogel is substantially free of laminin.

9. The method of claim 1 wherein the hydrogel is substantially free of heparan sulfate.

10. The method of claim 1 wherein the method further comprises administering the construct to a patient.

11. The method of claim 10, wherein the step of administering the construct further comprises implanting the construct into the patient.

12. The method of claim 11 wherein the construct comprises a hydrogel sponge with effective pore sizes ranging from 10 nanometers to 10 micrometers.

* * * * *